US008999643B2

United States Patent
Reddel et al.

(10) Patent No.: US 8,999,643 B2
(45) Date of Patent: Apr. 7, 2015

(54) METHODS AND ASSAYS FOR THE DETECTION OF ALTERNATIVE LENGTHENING OF TELOMERES (ALT) ACTIVITY IN CELLS

(75) Inventors: Roger Robert Reddel, St. Ives (AU); Jeremy David Henson, Castle Hill (AU)

(73) Assignee: Children's Medical Research Institute, Westmead, New South Wales (AU)

( * ) Notice: Subject to any disclaimer, the term of this patent is extended or adjusted under 35 U.S.C. 154(b) by 165 days.

(21) Appl. No.: 13/497,473

(22) PCT Filed: Sep. 21, 2010

(86) PCT No.: PCT/AU2010/001243
§ 371 (c)(1),
(2), (4) Date: Sep. 5, 2012

(87) PCT Pub. No.: WO2011/035375
PCT Pub. Date: Mar. 31, 2011

(65) Prior Publication Data
US 2012/0329047 A1   Dec. 27, 2012

(30) Foreign Application Priority Data
Sep. 22, 2009   (AU) .................................. 2009904602

(51) Int. Cl.
*C12Q 1/68*   (2006.01)
(52) U.S. Cl.
CPC ........ *C12Q 1/6883* (2013.01); *C12Q 2600/158* (2013.01); *C12Q 2600/112* (2013.01); *C12Q 2600/136* (2013.01)
(58) Field of Classification Search
None
See application file for complete search history.

(56) References Cited

FOREIGN PATENT DOCUMENTS

WO   WO-2008025481 A1   3/2008

OTHER PUBLICATIONS

Nabetani et al . Molecular Cell Biol. Nov. 17, 2008. 29(3): 703.*
Plantinga et al. Molecular Cancer Research. 2013. 11(6): 557-567.*
Wang R. C., et al., Homologous Recombination Generates T-Loop Size Deletions at Human Telomeres, Cell, Oct. 29, 2004, vol. 119, pp. 355-368.
Zellinger B, et al., Ku Suppresses Formation of Telomeric Circles and Alternative Telomere Lengthening in Arabidopsis, Molecular Cell, Jul. 6, 2007, vol. 27, pp. 163-169.
Nosek J., et al., Amplification of Telomeric Arrays via Rolling-circle Mechanism, The Journal of Biological Chemistry, Mar. 18, 2005, vol. 280, No. 11, pp. 10840-10845.
Groff-Vindman C., et al., Molecular and Cellular Biology, Recombination at Long Mutant Telomeres Produces Tiny Single- and Double-Stranded Telomeric Circles, Jun. 2005, vol. 25, No. 11, pp. 4406-4412.
International Search Report issued in PCT/AU2010/001243 on Nov. 29, 2010.
Henson, et al., DNA C-circles are specific and quantifiable markers of alternative-lengthening-of-telomeres activity, *Nature Biotechnology*., 2009, 27:12:1181-1185.

* cited by examiner

*Primary Examiner* — Carla Myers
(74) *Attorney, Agent, or Firm* — Blank Rome LLP

(57) ABSTRACT

The invention relates to methods and assays for the detection of active Alternative Lengthening of Telomeres (ALT) activity in cells. The methods and assays involve detecting or assaying for partially double-stranded telomeric circles wherein the presence of said circles is specific for cells comprising an active ALT mechanism. In some embodiments the methods find application in, inter alia, determining the level of ALT activity in a cell, determining the ALT status of a cancer in a subject, diagnosing and/or treating disease, determining disease status, analysis of treatment efficacy, and the identification of novel therapeutic agents.

18 Claims, 11 Drawing Sheets

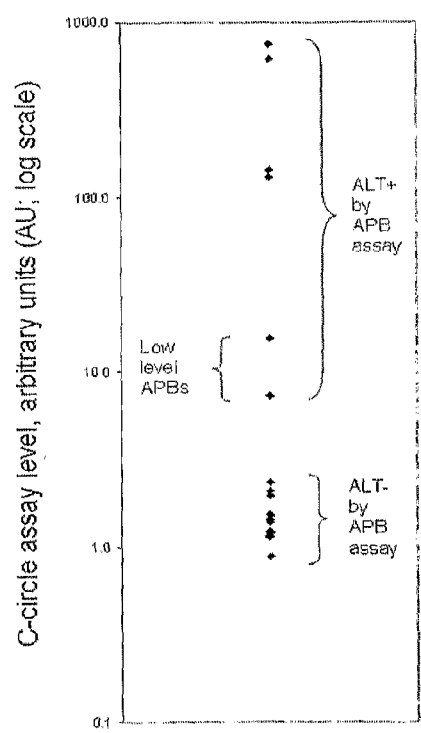 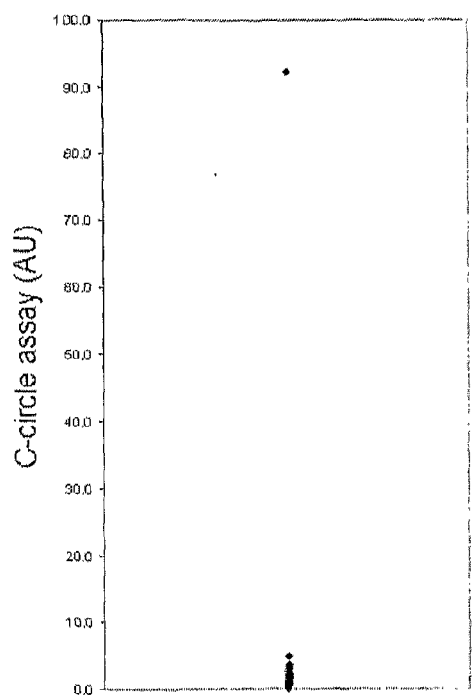
Figure 9                           Figure 10

SEQUENCE LISTING

```
<160> NUMBER OF SEQ ID NOS: 6

<210> SEQ ID NO 1
<211> LENGTH: 30
<212> TYPE: DNA
<213> ORGANISM: Artificial
<220> FEATURE:
<223> OTHER INFORMATION: Synthetic sequence
<220> FEATURE:
<221> NAME/KEY: repeat_unit
<222> LOCATION: (14)..(19)
<223> OTHER INFORMATION: repeat x 12

<400> SEQUENCE: 1
cccatatcac taaccctaac ctcaattccc                                          30

<210> SEQ ID NO 2
<211> LENGTH: 18
<212> TYPE: DNA
<213> ORGANISM: Artificial
<220> FEATURE:
<223> OTHER INFORMATION: Synthetic sequence

<400> SEQUENCE: 2
tgatatgggg ggaattga                                                       18

<210> SEQ ID NO 3
<211> LENGTH: 17
<212> TYPE: DNA
```

```
<213> ORGANISM: Artificial
<220> FEATURE:
<223> OTHER INFORMATION: Synthetic sequence

<400> SEQUENCE: 3
gtaaaacgac ggccagt                                                    17

<210> SEQ ID NO 4
<211> LENGTH: 18
<212> TYPE: DNA
<213> ORGANISM: Artificial
<220> FEATURE:
<223> OTHER INFORMATION: Synthetic sequence

<400> SEQUENCE: 4
acaggaaaca gctatgac                                                   18

<210> SEQ ID NO 5
<211> LENGTH: 23
<212> TYPE: DNA
<213> ORGANISM: Artificial
<220> FEATURE:
<223> OTHER INFORMATION: Synthetic sequence

<400> SEQUENCE: 5
gaagcaagau guuauagaad tdt                                             23

<210> SEQ ID NO 6
<211> LENGTH: 23
<212> TYPE: DNA
<213> ORGANISM: Artificial
<220> FEATURE:
<223> OTHER INFORMATION: Synthetic sequence

<400> SEQUENCE: 6
cucugguaug gacacagcud tdt                                             23
```

METHODS AND ASSAYS FOR THE DETECTION OF ALTERNATIVE LENGTHENING OF TELOMERES (ALT) ACTIVITY IN CELLS

This application is the national stage of International Application No. PCT/AU2010/001243, filed Sep. 21, 2010, which claims the benefit of Australian Patent Application No. 2009904602, filed Sep. 22, 2009.

FIELD OF THE INVENTION

The present invention relates generally to methods and assays for the detection of active Alternative Lengthening of Telomeres (ALT) activity in cells. More particularly, in vertebrate cells the methods and assays of the invention involve detecting partially double-stranded telomeric circles. Methods of the invention find application in, inter alia, disease diagnosis, disease status determination, analysis of treatment regime efficacy, and the identification of novel therapeutic agents.

BACKGROUND OF THE INVENTION

Somatic cells have a finite proliferative capacity. The role of telomeres in regulating cell division, in particular the number of cell divisions a cell lineage can undergo, is critical. Telomeres are repetitive DNA sequences, typically G-rich on one strand (C-rich on the complementary strand), at the termini of linear chromosomes. In human (and indeed most vertebrate) chromosomes telomeres comprise typically several thousand copies of the sequence $(5'\text{-TTAGGG-}3')_n$. Typically, telomeres shorten with each round of cell division, at least in part due to the incomplete replication of the ends of linear chromosomes. When telomeres become too short this evokes normal cellular DNA damage repair pathways. A complex series of biochemical and morphological changes ensues resulting in cell cycle arrest and cell death, either via replicative senescence or via programmed cell death such as apoptosis. Senescence and apoptosis each constitute major pathways for the regulation of cell proliferation. These processes are beneficial, for example, in the suppression of tumorigenesis and limiting disease progression more generally (see, for example, Collado et al., 2005). In pathological conditions characterised by aberrant cellular proliferation, such as cancer, the normal senescence and apoptotic pathways are circumvented enabling cells to become immortal.

Broadly speaking, two alternative telomere maintenance mechanisms are used by cancer cells to counteract the innate telomere loss that normally accompanies linear chromosome replication. The first involves synthesis of new telomeric DNA from an RNA template using the reverse transcriptase telomerase. Alternatively, telomeres may be maintained via a telomerase-independent process known as Alternative Lengthening of Telomeres (ALT) (Bryan et al., 1995; Bryan et al., 1997). The ALT mechanism involves recombination-dependent DNA replication using either the same telomere or another telomere, or possibly extrachromosomal telomeric DNA as the copy template (see, for example, Henson et al., 2002). ALT generates sudden, large increases in telomere length, consistent with either a long linear telomeric template or a rolling mechanism, such as rolling circle amplification (RCA).

Cells of a number of human tumours utilize ALT, especially those arising in brain, bone and connective tissue (see, for example, Bryan et al., 1997; Hakin-Smith et al., 2003; Henson et al., 2005; Ulaner et al., 2003; Villa et al., 2008), but the full extent of the role and importance of ALT in many cancers is yet to be fully elucidated. The prognosis for patients with an ALT[+] cancer is generally poor, with median survival ranging from 2 to 5 years.

Both telomerase and ALT represent attractive targets for anti-cancer treatment and there is an increasing recognition that for many cancers it will be desirable to have at our disposal therapies that are specific for ALT[+] cells and therapies that are specific for telomerase[+] cells. Cancer cells of a specific cancer type in one individual may utilise telomerase for telomere maintenance, whereas cells of the same cancer type in another individual may utilise ALT, and indeed cells within a single tumour may utilise different telomere maintenance mechanisms. It is also thought that cancer cells may have the capacity under certain conditions to switch between telomerase-induced telomere maintenance and ALT, raising the possibility that as telomerase-specific cancer therapies increase in clinical use, the prevalence of ALT[+] cancer cells may increase. Thus, with the development of ALT-specific and telomerase-specific therapies, it will become increasingly important to determine whether the cancer in any given individual is ALT[+] or telomerase[+].

There also remains the need for the identification and development of suitable therapeutic agents capable of inhibiting ALT. There is also a need for the identification and development of activators of ALT to induce cellular immortality and for application in, for example, research into aging. However hampering such efforts is that there is presently no enzyme activity or protein that is known to be specific for ALT.

To date, ALT activity has been demonstrated indirectly, for example by the maintenance of average telomere length over many population doublings in the absence of telomerase. The presence of ALT has also been deduced by observing rapid changes in the length of individual telomeres or other characteristics of ALT[+] cells, the presence of a highly heterogeneous telomere length distribution, increased telomeric recombination, and telomeric DNA in promyelocytic leukemia nuclear bodies. None of the current assays for ALT activity are suitable as a screen for ALT inhibitors, which requires a simple, definitive assay that is rapidly and linearly responsive to changes in ALT activity. Detection of ALT activity in cancer patients currently requires the availability of tumour specimens or biopsies, and the techniques available lack responsiveness and/or sensitivity, and are not generally suitable for use in routine pathology laboratories.

There is a clear need for the development of accurate, reliable and rapidly responsive assays of ALT activity, based on parameters that are specific for ALT[+] cells. As disclosed herein the present inventors have found that the presence of partially double-stranded telomeric DNA circles is a highly specific and quantitative marker for an active ALT mechanism within a cell.

SUMMARY OF THE INVENTION

According to a first aspect of the present invention there is provided a method for determining whether a cell possesses an active ALT mechanism, the method comprising assaying for the presence of partially double-stranded telomeric circles wherein the presence of said telomeric circles is specific for cells comprising an active ALT mechanism.

In embodiments in which the cell is a vertebrate cell, the partially double-stranded telomeric circles typically comprise repeats of the sequence $(CCCTAA)_n$ on the circular strand and of the sequence $(TTAGGG)_n$ on the linear strand. The partially double-stranded telomeric circles may comprise repeats of the sequence $(TTAGGG)_n$ on the circular strand and of the sequence $(CCCTAA)_n$ on the linear strand. The circular and/or linear strand may comprise variant and/or mutant telomeric repeat sequences. The circular and/or linear strand may further comprise non-telomeric sequences.

The cell may be a cancer cell.

The cell may be derived from a subject suffering from, suspected of suffering from, or predisposed to, a disease or condition associated with abnormal cellular proliferation. The disease or condition may be a cancer. The cancer may be selected from, for example, a sarcoma, a blastoma, a carcinoma, a mesothelioma or an astrocytoma. The sarcoma may be osteosarcoma, malignant fibrous histiocytoma, liposarcoma, synovial sarcoma, fibrosarcoma, chondrosarcoma, rhabdomyosarcoma or leiomyosarcoma. The blastoma may be neuroblastoma. The carcinoma may be a non-small cell lung carcinoma such as lung adenocarcinoma or a breast carcinoma. The mesothelioma may be peritoneal mesothelioma. The astrocytoma may be low-grade astrocytoma, anaplastic astrocytoma, or glioblastoma multiforme.

The partially double-stranded telomeric circles may be detected directly or indirectly. For example, detection may be indirect following rolling circle amplification using the circular strand of the partially double-stranded circles as template. In an embodiment, the detection comprises:
(a) optionally isolating DNA from the cell;
(b) incubating the DNA in the presence of a DNA polymerase and one or more dNTPs under suitable conditions such that polymerase-mediated extension from the incomplete (linear) strand generates concatemers of single-stranded telomeric DNA; and
(c) detecting the concatemers.

The concatemers may be detected by any suitable means such as, for example, hybridisation, sequencing, PCR, molecular beacons, nucleic acid enzymes such as DNA partzymes, or by incorporating suitably labelled dNTPs in incubation step (b).

The DNA polymerase may be, for example, φ29 DNA polymerase. Typically, wherein the partially double-stranded telomeric circles comprise repeats of the sequence $(CCCTAA)_n$ on the circular strand, the dNTPs consist of dATP, dGTP and dTTP, and optionally dCTP.

In accordance with the above aspect, the detection of the partially double-stranded telomeric circles may be detection of said circles present within the cell, or alternatively may comprise the detection of said circles in a biological sample, for example derived from a subject. Detection may be direct or indirect. The biological sample may comprise, for example, blood, urine, sputum, pleural fluid, peritoneal fluid, bronchial and bronchoalveolar lavage fluid, or a tissue section. The sample may be obtained, for example, by fine needle aspiration biopsy. The blood may be whole blood, blood serum or blood plasma.

A second aspect of the invention provides a method for determining the level of ALT activity in a cell, the method comprising assaying for the amount of partially double-stranded telomeric circles wherein the amount of said circles is indicative of the level of ALT activity in the cell.

The cell may be a cancer cell.

A third aspect of the invention provides a method for determining the ALT status of a cancer in a subject, the method comprising:
(a) obtaining a sample from the subject; and
(b) assaying the sample for the presence of partially double-stranded telomeric circles,
wherein the presence of said circles is indicative of the cancer cells having ALT activity and the absence of said circles is indicative of the cancer cells not possessing ALT activity.

The method may further comprise determining the amount of partially double-stranded telomeric circles in the sample to thereby quantify the level of ALT activity in the cancer cells and/or the amount or proportion of ALT[+] cells in the sample.

The cancer may be selected from, for example, a sarcoma, a blastoma, a carcinoma, a mesothelioma or an astrocytoma. The sarcoma may be osteosarcoma, malignant fibrous histiocytoma, liposarcoma, synovial sarcoma, fibrosarcoma, chondrosarcoma, rhabdomyosarcoma or leiomyosarcoma. The blastoma may be neuroblastoma. The carcinoma may be a non-small cell lung carcinoma such as lung adenocarcinoma, a breast carcinoma, gastric carcinoma, adrenocortical carcinoma, ovarian carcinoma or melanoma. The mesothelioma may be peritoneal mesothelioma. The astrocytoma may be low-grade astrocytoma, anaplastic astrocytoma, or glioblastoma multiforme.

A fourth aspect of the invention provides a method for diagnosing cancer, or predicting the onset thereof, in a subject, wherein the cancer displays ALT activity, the method comprising:
(a) obtaining a sample from the subject; and
(b) assaying the sample for the presence and/or amount of partially double-stranded telomeric circles,
wherein the presence and/or amount of said circles is indicative of the subject having cancer, or the likelihood of the onset of cancer in the subject.

By way of example only, the subject may be suspected of having cancer, may be predisposed or otherwise susceptible thereto, may have one or more high risk factors for developing cancer or may have a cancer predisposition syndrome such as Werner Syndrome, Rothmund-Thomson Syndrome or Li-Fraumeni Syndrome. The method may be employed as part of a screening program for such subjects, or a screening program for a broader population.

A fifth aspect of the invention provides a method for determining disease control in a subject suffering from a cancer displaying ALT activity, the method comprising:
(a) obtaining a sample from the subject; and
(b) assaying the sample for the presence of partially double-stranded telomeric circles,
wherein the presence of said circles is indicative of disease control in the subject.

Typically the subject may be undergoing, or have undergone, treatment for the cancer such as, for example, surgery, chemotherapy or radiotherapy.

The method may further comprise monitoring disease control in the subject over time comprising repeating steps (a) and (b) at least once over a period of time, and determining whether the presence and/or amount of said circles changes over the period of time.

A sixth aspect of the invention provides a method for evaluating the efficacy of a treatment regime in a subject suffering from a cancer displaying ALT activity, the method comprising:
(a) treating the subject with a suitable anti-cancer treatment regime for a period sufficient to evaluate the efficacy of the regime;
(b) obtaining a sample from the subject;
(c) assaying the sample for the presence and/or amount of partially double-stranded telomeric circles;
(d) repeating steps (b) and (c) at least once over a period of time; and (e) determining whether the presence and/or amount of said circles changes over the period of time,
wherein a change in the presence and/or amount of said circles is indicative of a'change in disease control in the subject and the degree of efficacy of the treatment regime.

A seventh aspect of the invention provides a method for designing a suitable treatment regime for a subject suffering from cancer, the method comprising determining the presence or absence of partially double-stranded telomeric circles, in a sample derived from the subject, wherein the presence of said circles is indicative an ALT[+] cancer such that an ALT-specific treatment regime is indicated.

The absence of said circles may be indicative of a telomerase[+] cancer such that a telomerase-specific treatment regime is indicated.

An eighth aspect of the invention provides a method for designing a suitable treatment regime for a subject suffering from a cancer displaying ALT activity, the method comprising monitoring the presence and/or amount of partially double-stranded telomeric circles, in a sample from the subject in accordance with any of the above aspects in the presence or absence of a treatment regime for treating the cancer, and adjusting the identity, timing and/or intensity of the treatment regime so as to reduce or eliminate said circles, wherein the reduction or elimination of said circles is indicative of an inhibition of ALT activity.

A ninth aspect of the invention provides a method for treating a subject suffering from a cancer displaying ALT activity, comprising administering to the subject a treatment regime designed in accordance with the seventh or eighth aspect.

A tenth aspect of the invention provides a method for identifying a compound suitable for modulating ALT activity in a cell, the method comprising;
(a) providing one or more cells displaying or capable of displaying ALT activity;
(b) determining the amount of partially double-stranded telomeric circles in accordance with any of the above aspects;
(c) contacting the one or more cells with a candidate compound; and
(d) determining the amount of said circles in accordance with any of the above aspects,
wherein a change in the amount of said circles between steps (b) and (d) is indicative of the ability of the candidate compound to modulate ALT activity.

A reduction in the amount of said circles between steps (b) and (d) is indicative of the ability of the candidate compound to inhibit ALT activity, whereas an increase in the amount of said circles between steps (b) and (d) is indicative of the ability of the candidate compound to activate ALT activity.

The candidate compound may be, for example, an anti-cancer agent, a putative anti-cancer agent or an anti-aging compound. An anti-aging compound includes an anti-cellular or -replicative senescence compound, or an anti-programmed cell death compound such as an anti-apoptotic compound.

It will be appreciated by those skilled in the art that whilst aspects and embodiments above may refer to the diagnosis, evaluation and treatment of cancer, these aspects and embodiments are also applicable to the diagnosis, evaluation and treatment of other diseases associated with aberrant cellular proliferation in which ALT activity is utilised by the diseased cells as a means of maintaining telomere length.

Methods embodied by the present invention are particularly suitable for the analysis of ALT activity in human cells and determining the level of ALT activity in human diseases, such as cancers. However the invention is not limited thereto and extends to the analysis of ALT in cells and subjects of any species comprising telomeric sequences at the termini of linear chromosomes. Typically the cells are eukaryotic cells, more typically vertebrate cells and more particularly mammalian cells.

BRIEF DESCRIPTION OF THE DRAWINGS

The present invention will now be described, by way of non-limiting example only, with reference to the accompanying drawings in which:

FIG. 9 is a scatterplot of CC Assay (C-circle assay) levels for 16 soft tissue sarcomas (STS), which had their ALT status previously determined by the APB assay. CC Assay levels are plotted on a logarithmic scale. The CC Assay levels clearly distinguish ALT[+] from ALT[−] STS. The STS with low ALT activity as determined by both the APB assay and the CC Assay could be due to a uniform low level or an ALT[+] subpopulation which has its ALT activity diluted by an adjacent ALT[−] population.

FIG. 10 is a scatterplot of CC Assay (C-circle assay) levels for 27 glioblastoma multiforme tumours, which had their ALT status previously determined by the TRF assay. The CC Assay levels clearly distinguish ALT[+] from ALT[−] glioblastoma multiforme.

Figure 1:
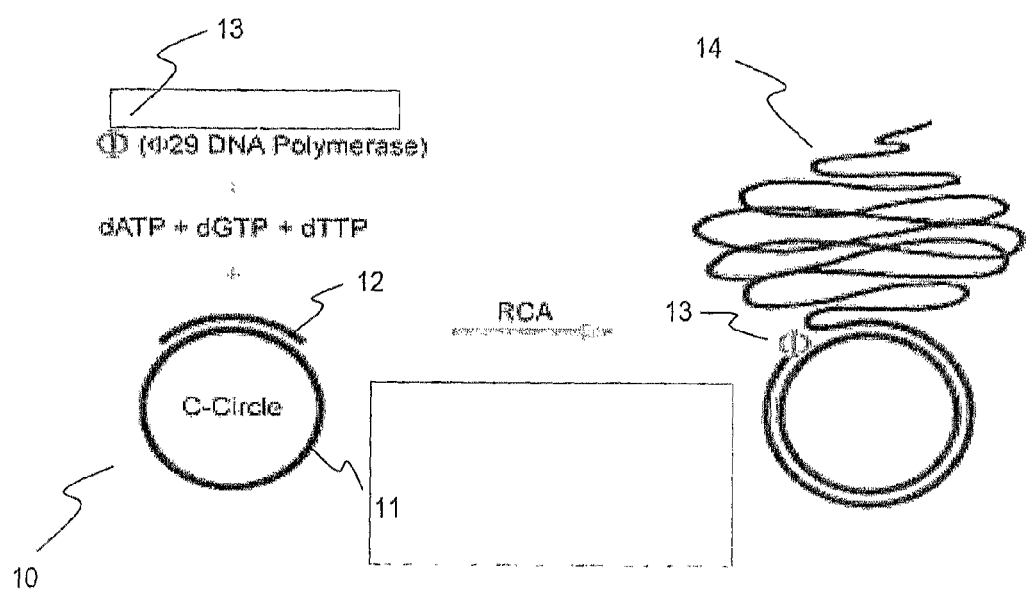
FIG. 1 is a schematic illustration of an assay utilising rolling circle amplification (RCA) in accordance with an embodiment of the invention.

The sequences of specific oligonucleotides and primers used herein (see Examples) are provided in a formal Sequence Listing appearing at the end of the specification. Those skilled in the art will appreciate that the sequences provided are exemplary only and do not limit the scope of the present disclosure in any way.

DETAILED DESCRIPTION OF THE INVENTION

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

The articles "a" and "an" are used herein to refer to one or to more than one (i.e., to at least one) of the grammatical object of the article. By way of example, "an element" means one element or more than one element.

The term "ALT" as used herein refers to the process of telomere maintenance known as "Alternative Lengthening of Telomeres" or telomerase-independent telomere maintenance. Thus, in its broadest context, "ALT" refers to a means or mechanism of maintaining the length of telomeres (preventing telomere shortening) that is independent of the activity of telomerase. Often referred to as the "ALT mechanism", it will be appreciated that the invention is not limited by any one specific mechanism by which ALT may operate in a cell to maintain telomeres. Thus the term "mechanism" is used generally in this context rather than referring to a specific biochemical mechanism or pathway by which an "ALT mechanism" operates. There may indeed be more than one specific pathway by which ALT operates.

By "ALT[+]" is meant that a cell displays or possesses ALT activity (i.e. is an 'ALT active' cell), whereas the term "ALT [−]" indicates that the cell does not display or possess ALT activity (i.e. is an 'ALT negative' cell). Similar meanings apply herein for the terms "telomerase[+]" and "telomerase [−]", indicating that the enzyme telomerase is active or not active, respectively, in a cell.

As used herein the term "associated with" when used in the context of a disease or condition "associated with" aberrant cellular proliferation means that the disease or condition may result from, result in, be characterised by, or otherwise associated with unregulated or otherwise excessive cellular proliferation. Thus, the association between the disease or condition and excessive cellular proliferation may be direct or indirect and may be temporally and/or spatially separated.

As used herein, the term "disease control" means the status of a disease or condition, typically in light of intervention to treat the disease or condition. Thus "disease control" describes the range and severity of symptoms and conditions experienced and suffered by patients as a result of their disease. Disease control effectively provides a measure at a given point in time of the disease status of an individual, reflecting both current therapeutic treatment regimes used by the individual and the individual's recent experiences.

As used herein the term "effective amount" includes within its meaning a non-toxic but sufficient amount or dose of an agent or compound to provide the desired effect. The exact amount or dose required will vary from subject to subject depending on factors such as the species being treated, the age and general condition of the subject, the severity of the condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

As used herein the terms "nucleic acid", "nucleotide sequence", "oligonucleotide" and "primer" designate any nucleic acid-based molecule, including DNA, cDNA, RNA, mRNA, cRNA, PNA or any combination thereof. Thus, a nucleic acid molecule, an oligonucleotide or a primer may comprise naturally occurring nucleotides, non-naturally nucleotides or a combination thereof.

As used herein the term "oligonucleotide" refers to a single-stranded sequence of deoxyribonucleotide or ribonucleotide bases, known analogues of natural nucleotides, or mixtures thereof. Oligonucleotides are typically short (for example less than 100 nucleotides in length) sequences which may be prepared by any suitable method, including, for example, direct chemical synthesis or cloning and restriction of appropriate sequences. Typically in the context of the present invention an oligonucleotide is designed to recognise and bind to a specific complementary nucleotide sequence located within another nucleic acid molecule. An oligonucleotide may also include bases in addition to those required to hybridise to the complementary sequence. The oligonucleotide may or may not be able to act a primer for polymerase-mediated extension. Not all bases in an oligonucleotide need be complementary to the sequence to which the oligonucleotide is designed to bind; the oligonucleotide need only contain sufficient complementary bases to enable the oligonucleotide to recognise and bind to that sequence. The oligonucleotide sequence may be an unmodified nucleotide sequence or may be chemically modified or conjugated by a variety of means known to those skilled in the art.

As used herein the term "partially double-stranded telomeric circles" means in its broadest sense DNA molecules comprising a complete, or uninterrupted, circular strand (a "closed circular strand") and a linear strand, wherein the circular strand comprises C-rich or G-rich telomeric DNA sequence and the linear strand comprises complementary G-rich or C-rich telomeric DNA sequence. In the context of the present disclosure, partially double-stranded telomeric circles comprising C-rich telomeric sequences (for example the telomeric repeat $(CCCTAA)_n$) on the circular strand are referred to as "C-circles" and partially double-stranded telomeric circles comprising G-rich telomeric sequences (for example the telomeric repeat $(TTAGGG)_n$) on the circular strand are referred to as "G-circles". Within the context of the present definition, the term "linear" is to be given its broadest interpretation, meaning 'not circular', whilst "circular" means a complete, uninterrupted circular DNA strand. Thus, the linear strand may be of a fragment or segment of DNA of any length that is not a complete or uninterrupted circle, the linear strand comprising a 3' end hybridised to the circular strand and hence able to be extended by a polymerase in a rolling circle replication/amplification mechanism using the closed circular strand as a template, or alternatively the linear strand comprising a 3' end that is not hybridised to the circular strand but which is processed by a polymerase or other enzyme complex so as to render it capable of being extended by a polymerase in a rolling circle replication/amplification mechanism using the closed circular strand as a template. For example, the linear strand may be a short fragment with minimum nucleotides sufficient to enable hybridisation to the circular strand to generate a short double-stranded region, or may comprise sufficient complementary sequence to the circular strand such that the double-strandedness is almost complete between the circular and the linear strand with the linear strand containing a nick, and all intermediates in between. The linear strand may also have one or more 5' tails that are not hybridised with the circular strand. The telomeric sequences in the circular and/or linear strand may be variant or mutated telomeric repeat sequences. The circular and/or linear strand may comprise variant and/or mutated telomeric repeat sequences in addition to canonical telomeric repeat sequences. By "variant" and "mutated" is meant that the telomeric sequences differ from canonical telomeric sequences at one or more nucleotide positions, by either base insertion, deletion or substitution. Each or both of the circular and linear strands may also comprise non-telomeric sequences (such that the strand as a whole may or may not be C-rich or G-rich). The strands typically contain sufficient telomeric sequences (or variant or mutated telomeric sequences with sufficient homology to the genomic telomeric sequences) to enable hybridisation to telomeric DNA, typically under physiological conditions. Thus, within the context of the above definition, the circular and linear strands need only comprise telomeric sequences and need not be composed predominantly or solely of telomeric sequences in order to be termed "telomeric". Also within the context of this definition, the term "partially" encompasses any extent of double-strandedness that is not complete double-strandedness.

As used herein the term "primer" refers to an oligonucleotide that binds to a specific region of a single stranded template nucleic acid molecule and initiates nucleic acid synthesis via an enzymatic reaction, extending from the 3' end of the primer and complementary to the sequence of the template molecule. By convention, primers are typically referred to as 'forward' and 'reverse' primers, one of which is complementary to a nucleic acid strand and the other of which is complementary to the complement of that strand.

As used herein the term "sample" refers to any biological sample that comprises nucleic acid molecules, typically comprising DNA and/or RNA. Samples may be tissues, cells or extracts thereof, or may be purified samples of nucleic acid molecules. Use of the term "sample" does not necessarily imply the presence of sequences to be assayed in accordance with the methods described herein within in the sample.

With reference to a disease such as cancer, the term "status" as used herein refers to the disease state or disease activity in a given subject at a given time. "Status" correlates with the presence or absence of partially double-stranded telomeric circles as defined herein. The absence of, or a reduction over time of, the amount of said partially double-stranded telomeric circles may be indicative of an inactive disease status, for example quiescence of the disease or remission. The presence of, or an increase over time of, the amount of said partially double-stranded telomeric circles may be indicative of an active disease status, which may indicate, for example growth or spread in the size and/or extent of a tumour, or correlate with the subject experiencing one or more symptoms associated with the disease.

As used herein the term "treatment" and variations thereof refer to any and all uses which remedy a condition or symptoms, prevent the establishment of a condition or disease, or otherwise prevent, hinder, retard, or reverse the progression of a condition or disease or other undesirable symptoms in any way whatsoever. Thus terms "treating" and the like are to be considered in their broadest context. For example, treatment does not necessarily imply that a patient is treated until total recovery. Treatment also includes amelioration of the symptoms of a particular disorder or preventing or otherwise reducing the risk of developing a particular disorder.

To date, assays for ALT activity in cells have been limited to indirect assays of factors or phenomena associated with ALT or the effects of ALT. Such assays may measure or observe, for example, the presence of a highly heterogeneous telomere length distribution by measuring terminal restriction fragments (TRFs), increased telomeric recombination, the presence of telomeric DNA or telomere binding proteins in promyelocytic leukemia (PML) nuclear bodies, double-stranded extrachromosomal telomeric circles (t-circles), increased postreplicative telomeric exchanges, and increased instability of specific minisatellite repeats. However the attributes measured are indirectly associated with ALT and in many instances may have alternative explanations or causative factors. For example long, heterogeneous telomeres and PML nuclear bodies containing telomeric DNA have also been shown to occur in telomerase-positive cells and to be absent in some ALT[+] cells. Thus presently available assays typically suffer from a lack of specificity for ALT and hence a lack of reliability. Increased telomeric sister chromatid exchange and t-circles can also occur independently of ALT.

The need for a simple, sensitive, specific and rapidly responsive assay for ALT activity is demonstrated by the fact that for an increasing number of proteins (for example MUS81, Rad51D, FANCD2, Topo IIIα, BLM and FEN1) their significance for the ALT mechanism is questioned. For example, it is unclear if these proteins directly contribute to ALT, or are indirectly required in ALT[+] cells. Furthermore, these proteins play other (often essential) cellular roles and often inhibition markedly reduces viability of ALT cells making assessment of ALT activity difficult.

As described herein the inventors have for the first time identified an ALT[+]-specific marker. Specifically the inventors have found that partially double-stranded telomeric circles are specific for cells with an active ALT mechanism. These circles appear shortly after activation of ALT and rapidly disappear upon inhibition of ALT. Moreover, the levels of these circles are shown to correlate with the level of ALT activity.

Thus, described herein for the first time is a reliable, specific and quantitative assay for ALT activity based on the detection and/or quantification of partially double-stranded telomeric circles. The inventors' novel findings open the way for the development of an accurate, specific and efficient alternative to presently available methodology for determining ALT activity.

Without wishing to be bound by any one theory, the inventors speculate that in view of their circular nature, precise specificity and short half-life, partially double-stranded telomeric circles are directly linked to the ALT mechanism and are likely to be direct intermediates in ALT[+] rolling circle amplification, rather than byproducts.

According to one aspect, the present invention provides a method for determining whether a cell possesses an active ALT mechanism, the method comprising assaying for the presence of partially double-stranded telomeric circles, wherein the presence of said circles is specific for cells comprising an active ALT mechanism.

In embodiments in which the cell is a vertebrate cell, the partially double-stranded telomeric circles typically comprise repeats of the sequence $(CCCTAA)_n$ on the circular strand and comprise the sequence $(TTAGGG)_n$ on the linear strand, or alternatively repeats of the sequence $(TTAGGG)_n$ on the circular strand and comprise the sequence $(CCCTAA)_n$ on the linear strand.

Methods as described herein find application, inter alia, in the development of assays for the diagnosis of ALT[+] diseases, assays to evaluate the therapeutic response of ALT[+] diseases to treatment and optimise such treatment, and assays to monitor the progression and development of ALT[+] diseases. In addition it will be appreciated that the ability to reliably and specifically measure ALT activity opens the way for the development of ALT-specific therapeutics.

In accordance with an embodiment as described and exemplified herein, a simple ALT activity assay has been developed in which partially double-stranded telomeric circles are detected via the initiation of rolling circle amplification and the subsequent analysis of the products of such amplification. Rolling circle amplification is a simple and sensitive technique for detecting circular DNA. Rolling circle amplification is a naturally occurring replicative process well known to those skilled in the art that is exploited in a variety of research applications (see, for example, Dean et al., 2001; the disclosure of which is incorporated herein in its entirety) and techniques for rolling circle amplification are well within the skills and capabilities of those skilled in the art. The rolling circle amplification is typically carried out in the presence of a suitable DNA polymerase and deoxyribonucleotides. In some circumstances rolling circle amplification offers advantages over other detection techniques available, for example the simple isothermic polymerase incubation required offers convenience for routine pathology laboratory application. However in some circumstances it may be desirable or necessary to use alternative means of detecting partially double-stranded telomeric circles, for example PCR, sequencing, hybridisation, molecular beacons, nucleic acid enzymes such as DNA partzymes. Techniques for carrying out alternative detection methods are well known to, and well within the skills and capabilities of, the skilled addressee. Those skilled in the art will also appreciate that the amount of product, or the rate of generation of product, produced by the rolling circle amplification reaction may be enhanced, for example, by the addition of specific primers to multiply prime on the rolling circle, thereby making the assay faster and/or more sensitive.

A schematic representation of an assay for the detection of partially double-stranded telomeric circles based on rolling circle amplification in accordance with embodiments of the present invention is shown in FIG. 1. It should be noted that one exemplification of partially double-stranded telomeric circles to which the present invention relates is illustrated in FIG. 1, but that the application of embodiments of the invention is not limited to this single exemplification. Rather, all partially double-stranded telomeric circles, as defined herein, are amenable to detection and quantitation by the methods described. Returning to FIG. 1, a partially double-stranded telomeric circle (10) comprises a complete (intact) circular strand (11) and a short linear segment (12) annealed to circular strand (11) so as to form a short double-stranded region. The partially double-stranded telomeric circle shown in FIG. 1 is a "C-circle" in which the circular strand (11) comprises the telomeric sequence $(CCCTAA)_n$, and linear segment (12) comprises the sequence complementary to a region of the circular strand. In performing the assay, C-circle (10) is incubated with φ29 DNA polymerase (13) in the presence of the dNTPs dATP, dGTP and dTTP (optionally including dCTP) under conditions such that φ29 DNA polymerase initiates second strand synthesis at the 3' end of the linear segment (12) with circular strand (11) acting as template. The result is the generation of long, linear concatemers (14) of single-stranded telomeric DNA. These concatemeric products may be detected by any suitable means, such as for example, hybridisation with a suitably labelled (CCCTAA)$_n$ probe, sequencing or PCR. Alternatively, detection may be achieved, for example, by means of providing suitably labelled and detectable dNTPs for incorporation by the polymerase.

φ29 DNA polymerase is one example of a suitable polymerase for use in accordance with embodiments of the invention. φ29 DNA polymerase is a highly processive polymerase with strand displacement ability that usually produces rolling circle amplification products≥70 kb in length. However those skilled in the art will recognise that other polymerases having similar characteristics may also be used and are contemplated herein. The deoxyribonucleotides (dNTPs) are typically selected from dATP, dGTP, dTTP and dCTP although the exact dNTPs to be employed will depend on the sequence of the partially double-stranded telomeric circles. For example, where the circular strand consists of repeats of the telomeric sequence CCCTAA, the rolling circle amplification may be conducted using the DNA polymerase in the presence of dATP, dGTP and dTTP only.

As shown in FIG. 1, by virtue of the linear segment providing a short double-stranded region of the circular DNA, rolling circle amplification may advantageously be conducted without requiring the provision an exogenous primer. Rather, the sequence of the linear segment (12) acts as the primer from which φ29 DNA polymerase-mediated strand synthesis is initiated.

As exemplified herein, an assay performed in accordance with methods described herein (and as shown schematically in FIG. 1) is sensitive, proving capable of detecting partially double-stranded telomeric circles in nanogram quantities of genomic DNA from ALT[+] cells, and is linear over the range 1 to 32 ng. Also as exemplified, partially double-stranded telomeric circles detected by the assay correlated precisely with ALT activity in a panel of 38 cell lines and cell strains of disparate origins, were not significantly increased by ALT independent generation of t-circles, correlated temporally with activation of ALT, and decayed rapidly following inhibition of ALT. Partially double-stranded telomeric circles are therefore specific for ALT[+] cells, and the methods and assays described herein provide the first quantitative measures of ALT activity levels. Further exemplified herein is the finding that partially double-stranded telomeric circles were detected in blood from ALT[+] osteosarcoma patients, suggesting that assays of such circles have clinical utility for diagnosis and management of ALT[+] tumours.

In accordance with the methods described herein the presence and/or amount of partially double-stranded telomeric circles may be analysed from isolated cells. Biological samples derived from subjects may also be used in accordance with the methods. A biological sample for use in accordance with embodiments of the invention may comprise one or more fluid or tissue samples, including, for example, blood, urine, sputum, pleural fluid, peritoneal fluid, bronchial and bronchoalveolar lavage fluid, and tissue sections. The sample may comprise fresh, frozen or otherwise stored biological material. The sample may be obtained by fine needle aspiration biopsy thereby enabling the analysis of multiple sections, for example, from the same tumour or diseased tissue. In some circumstances, the sample may undergo treatment, incubation or culturing after extraction from the subject. Typically, biological samples employed in accordance with the invention include blood. The blood may comprise whole blood, serum or more typically plasma. Thus, embodiments of the invention contemplate the development and implementation of simple, blood-based tests for ALT activity carried out in accordance with methods described herein.

In some embodiments genomic DNA may be extracted from cells prior to analysis. Alternatively, cells may otherwise be treated to make DNA available for analysis, for example a cell lysate could be used with or without denaturation or digestion of cellular proteins. Analysis may also take place in situ after permeabilisation of cells with or without prior fixation and/or crosslinking. Techniques for fixation, crosslinking and permeabilisation are well known to those skilled in the art.

Diseases amenable to analysis and/or treatment using the methods and assays described herein may be any diseases in which an ALT mechanism is utilised as a means of telomere maintenance. In particular embodiments as described and exemplified herein the diseases are cancers, but those skilled in the art will appreciate that the scope of the present disclosure is not so limited. By way of example only, the cancer may be sarcoma, a blastoma, a carcinoma, a mesothelioma or an astrocytoma. The sarcoma may be, for example, an osteosarcoma, malignant fibrous histiocytoma, liposarcoma, synovial sarcoma, fibrosarcoma, chondrosarcoma, rhabdomyosarcoma or leiomyosarcoma. The blastoma may be, for example, neuroblastoma. The carcinoma may be, for example, a non-small cell lung carcinoma such as lung adenocarcinoma, a breast carcinoma, gastric carcinoma, adrenocortical carcinoma, ovarian carcinoma or melanoma. The mesothelioma may be, for example, peritoneal mesothelioma. The astrocytoma may be, for example, low-grade astrocytoma, anaplastic astrocytoma, or glioblastoma multiforme. It will be appreciated that the scope of the present invention is not limited to the exemplified cancers and tumours. Additional cancer and tumours, and indeed additional diseases or conditions characterised by or associated with aberrant cellular proliferation may be found to utilise ALT as a means of telomere maintenance. Those skilled in the art will appreciate that the methods and assays described herein are applicable to any diseases or conditions characterised by or associated with aberrant cellular proliferation that utilise ALT as a means of telomere maintenance. Further, embodiments of the invention find application in the assessment, management and cancer diagnosis in subjects with tumour predisposition syndromes such as, for example, Werner Syndrome, Rothmund-Thomson Syndrome and Li-Fraumeni Syndrome.

Embodiments of the invention described herein provide for the diagnosis of ALT[+] diseases such as cancers and in the prediction of the likelihood of onset of ALT[+] diseases. Also provided are assays in which the determination of ALT activity may be used as a screening test for subjects at risk of developing or ALT[+] diseases. For example, such subjects may be identified as belonging to a group at high risk of developing a particular disease, such as by virtue of genetic predisposition, family history, or having or being exposed to one or more high-risk factors (e.g. biochemical, behavioural and environmental). For example, a subject may have a tumour predisposition syndrome such as Werners, Rothmund-Thomson or Li-Fraumeni Syndrome (in which ALT[+] tumours have been found (Henson, 2006)), or may be at increased risk of non-small cell lung carcinoma; 85% of cancers from the lungs and bronchi are non-small cell lung carcinomas and 8% of these are ALT[+] (Henson, 2006). Alternatively, disease screening programs of the broader population may also be employed using methods as disclosed herein.

Embodiments as described herein provide methods and assays for evaluating the status of a disease, such as cancer, in a subject, monitoring the status of the disease in a subject over time, evaluating the efficacy of a treatment or disease management regime and designing an appropriate treatment or disease management regime for an individual. For example, methods and assays of the invention may comprise determining whether the level of partially double-stranded telomeric circles in a suitable sample obtained from a subject suffering from a disease associated with ALT activity is within a predetermined range indicative of satisfactory control or management of the disease. A level outside of the predetermined range may indicate that the subject's disease treatment or management needs to be modified to improve disease control or that the subject should otherwise be placed on a suitable treatment regime. Similarly, a relative change in the level of partially double-stranded telomeric circles over time may also be indicative of either satisfactory control or management of the disease, or the need to modify or improve disease treatment and/or management.

The analysis may be repeated one or more times over a given period of time to monitor disease status in the subject over time. Determination of the disease status in a subject, in particular the monitoring of status over time, also facilitates decision making with respect to the most appropriate intervention or treatment regime for an individual subject. Similarly, detection of the presence or absence of partially double-stranded telomeric circles in a sample allows a determination of whether a disease is ALT[+] or telomerase[+], thereby influencing the therapy to be administered.

For ALT[+] diseases the treatment regime will typically be tailored so as to obtain a reduction in the level of partially double-stranded telomeric circles over time, thereby correlating with an inhibition of ALT activity or the killing of ALT[+] cells. Upon initiation of the treatment regime there may be an initial increase in the level of partially double-stranded telomeric circles, indicative on cell death, followed by a reduction in levels of such circles over time indicative of a reduction in the prevalence of ALT[+] disease cells. For example, this may comprise introducing a new treatment regime or modifying an existing regime with a view to improving disease symptoms or other parameters. The modification of a regime may be modification with respect to any one or more of a variety of factors, such as the nature of any existing medication, the dosage thereof, the timing of administration and/or any supplementary disease management strategies. Such decision making with respect to treatment regimes will vary from case to case and the determination of the most appropriate strategy is well within the expertise and experience of those skilled in the art.

By way of example, ALT activity is currently the best prognostic indicator for glioblastoma multiforme (Hakin-Smith et al., 2003) and is correlated with three fold increased median survival, although this survival is still poor. Whether blood or tumour sample based, an assay conducted in accordance with methods described herein has the potential to allow routine identification of the ALT[+] group in glioblastoma multiforme patients. Also by way of example, approximately 50% of osteosarcomas are ALT[+] (Ulaner et al., 2003; Henson et al., 2005) and ALT activity does not appear to affect response to current chemotherapy regimes. Response to preoperative chemotherapy is a major prognostic factor in osteosarcoma, however currently it can only be determined retrospectively by histological analysis of tumours removed by surgical resection, after completion of preoperative chemotherapy. The development of a specific assay to determine tumour resistance during preoperative chemotherapy would allow a more aggressive or targeted preoperative treatment regime to be instituted, that may be more successful in killing tumour cells and increase patient survival. Levels of plasma DNA can decrease markedly in cancer patients after successful therapy, and conversely can persist at high levels or increase with a lack of response to treatment. Further, in the context of the present disclosure, the efficacy of a particular treatment in killing tumour cells may also be evaluated where tumour cell death temporarily leads to an increase in the amount of partially double-stranded telomeric circles in the plasma over the period of cell death (for example apoptosis or necrosis). Thus, a quantitative blood test for ALT activity would assist the determination of the level of ALT[+] osteosarcoma cells surviving each chemotherapy cycle. An initial increase in the amount of partially double-stranded telomeric circles may be observed, indicative on cell death, which may be followed by a reduction in amounts of such circles over time indicative of a reduction in the abundance of ALT[+]osteosarcoma cells remaining. The information obtained from a quantitative blood test would then allow tailoring of preoperative chemotherapy to increase survival in the non-responsive and ALT[+] patient groups.

Those skilled in the art will appreciate that the evaluation of the efficacy of a disease therapy may be determined within the context of a clinical trial, in which case it may be desirable to stratify subjects undergoing the trial in the event that the therapy being trialled is more effective against either ALT[+] or ALT[−] diseases than against the other. Embodiments of the present invention therefore contemplate the use of an assay as described herein for the determination of the ALT status of a cancer in a subject or subject group, which stratification may be used to remove poor responding subjects or subject groups from the trial.

A treatment regime for the treatment/management of a disease associated with ALT activity in a subject in accordance with a method of the invention may involve administration of any medications commonly utilised in the treatment of the disease in question, for example one or more chemotherapeutic agents or radiotherapy in the case of cancer. The treatment regime may comprise the administration of a number of drugs simultaneously, sequentially, or in combination with each other. The type of drug(s) administered, dosage, and the frequency of administration can be determined by medical physicians in accordance with accepted medical principles, and will depend on factors such as the severity of the disease, the age and weight of the subject, the medical history of the subject, other medication being taken by the subject, existing ailments and any other health related factors normally considered when determining treatments.

Also provided herein are methods for identifying compounds and agents capable of modulating ALT activity based on detecting the presence or absence of, or changes in the level of, partially double-stranded telomeric circles as disclosed herein. Compounds and agents so identified may be inhibitors or activators of ALT. In a particular aspect, there is provided a method for identifying a compound suitable for modulating ALT activity in a cell, the method comprising: providing one or more cells displaying or capable of displaying ALT activity; determining the amount of partially double-stranded telomeric circles in accordance with any of the above aspects; contacting the one or more cells with a candidate compound; and determining the amount of said circles in accordance with any of the above aspects, wherein a change in the amount of said circles between determinations is indicative of the ability of the candidate compound to modulate ALT activity. A reduction in the amount of said circles is indicative of the ability of the candidate compound to inhibit ALT activity, whereas an increase in the amount of said circles is indicative of the ability of the candidate compound to activate ALT activity. Where the method is for the identification of an ALT inhibitor, the one or more cells provided are typically ALT[+]. Where the method is for the identification of an activator of ALT, the one or more cells provided may be ALT[+] or ALT [−]; in the case of ALT[+] cells an increase in partially double-stranded telomeric circles being indicative of the ability of the compound to activate ALT, and in the case of ALT[−] cells the appearance of partially double-stranded telomeric circles being indicative of the ability of the compound to activate ALT.

All essential components required for detecting partially double-stranded telomeric circles as disclosed herein in accordance with methods of the present invention may be assembled together in a kit. The kits may include appropriate components for detecting and quantifying partially double-stranded telomeric circle levels, appropriate positive and negative controls, dilution buffers, reagents (e.g. dNTPs; enzymes), primers and the like. Such reagents, buffers, controls and the like may be standardised so as to be suitable for use on any one of a number of devices known to those skilled in the art for the analysis of samples such as blood samples. Kits may also comprise devices and/or software to facilitate the employment of methods disclosed herein, for example including suitable computer software to determine or calculate a prognosis based on determined partially double-stranded telomeric circle levels. Typically, the kits comprise instructions for performing the methods of the present invention, optionally together with educative information and for treatment recommendations based on the results obtained using methods and kits of the present invention.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

It will be appreciated by persons skilled in the art that numerous variations and/or modifications may be made to the invention without departing from the spirit or scope of the invention as broadly described. The present embodiments are, therefore, to be considered in all respects as illustrative and not restrictive.

The present invention will now be described with reference to the following specific examples, which should not be construed as in any way limiting the scope of the invention.

EXAMPLES

General Methods

Patient Samples

Patient specimens were acquired with approval of the Human Research Ethics Committee of Children's Hospital Westmead, Whole blood specimens were provided by CHW Tumour Bank (−80° C. storage). Skin sample LFS-05, from a 37 year old Li-Fraumeni Syndrome patient was provided by kConFab; the origin of pre- and post-crisis fibroblasts cultured from this skin was confirmed by CellBank Australia using short tandem repeat profiling.

DNA Extraction and Quantitation

DNA from cell pellets was extracted by lysis with 2% SDS buffer and protein digested with 100 µg/ml Pronase protease (Sigma). After SDS and protein were salt precipitated, DNA was ethanol precipitated from the supernatant. DNA for Example 2 and from whole blood was extracted using QIAamp DNA Blood Mini Kit (Qiagen). Plasma from freshly collected blood was purified twice by centrifugation at 4° C. for 10 min, first at 1,600×g then at 16,000×g, flash frozen, stored at −80° C. and DNA extracted using the QIAamp UltraSens Virus Kit (Qiagen). Both ss and dsDNA were quantitated on a Qubit Fluorometer (Invitrogen).

Nuclease Treatment of DNA

Duplex Specific Nuclease (DSN; Evrogen) 40 U/µg, λ Exonuclease (NEB) 12.5 units/µg, Exonuclease I (NEB) at 100 U/µg and Exonuclease V (DNase, ATP-dependent; USB) at 30 U/µg were used according to the manufacturers' instructions. Whole blood linear DNA was removed by HinfI and RsaI restriction enzyme (NEB) pretreatment, repeated digestion with 0.15 U/µg λ Exonuclease and 1.5 U/µg Exonuclease 1, and finally, 60 U/sample Exonuclease V.

C-Circle Assay ("CC Assay")

Where appropriate genomic DNA was digested with 4 U/µg HinfI and RsaI restriction enzymes (NEB) and 25 ng/µg RNase (DNase free; Roche). Alternatively, in some experiments (Example 5) vortexing of the sample replaced the need for restriction enzyme digestion or RNase treatment. All DNA solutions were stored in 10 mM Tris [pH 7.6] at −80° C. Sample, 10 µl, was combined with 10 µl 0.2 mg/ml BSA, 0.1% Tween, 1 mM each dATP, dGTP and dTTP, 1× φ29 Buffer and 7.5 units φ29 DNA Polymerase (NEB) and incubated at 30° C. for 8 hr then 65° C. for 20 min. Only when stated, 1 mM dCTP was also included in the polymerase reaction. For quantitation, the CC Assay was performed in triplicate. Reaction products were diluted to 60 µl with 2×SSC and dot blotted onto a 2×SSC soaked Biodyne B nylon membrane (Pall). DNA was UV-cross-linked onto the membrane which was then hybridized at 37° C. with end-labelled $^{32}$P-(CCCTAA)$_3$ and PerfectHyb Plus hybridization buffer (Sigma). Exposure was optimized for the linear range of the phosphor screen which was scanned on a STORM 860 optical scanner with ImageQuant software (Molecular Dynamics), using edge subtraction for background correction. For size separation, reaction products were electrophoresed in 0.6% SeaKem Gold agarose (Lonza)—0.5× Tris-borate-EDTA at 1.75 V/cm for 12 hr. The gel was dried under vacuum at 60° C., washed in 2×SSC and incubated for 2 hr at 37° C. with 5×SSC, 5×Denhardt's solution, 0.5 mM tetrasodium pyrophosphate and 10 mM disodium hydrogen orthophosphate, before addition of end-labelled $^{32}$P-(CCCTAA)$_3$ and incubated overnight. The gel was washed with 0.1×SSC at 37° C. and imaged as for the dot blot membrane.

C96 C-Circles and M13 DNA

C96 C-circles were created by circularizing the 96 base oligonucleotide 5'-CCCATATCACTAA(CCCTAA)$_{12}$CCT-CAATTCCC-3' (SEQ ID NO:1) using linker 5'-TGATATGGGGGAATTGA-3' (SEQ ID NO:2) and T4 DNA Ligase (NEB). Unligated oligonucleotide and free linker was digested twice with 80 U Exonuclease I (NEB). Bound linker acted as a primer in the CC Assay for C96, M13 circles, M13 mp18 ssDNA (NEB) were primed with 5'-GTAAAACGACGGCCagt-3' (SEQ ID NO:3; thiophosphate linkages between the three 3' terminal nucleotides) as previously described (Dean et al., 2001), and linear ssDNA was digested twice with 80 U Exonuclease I. Primed M13 circles were used in the CC Assay with dCTP added to the reaction mix and probed with 5'-ACAGGAAACAGCTATGAC-3'(SEQ ID NO:4).

Telomere Maintenance Status

Terminal Restriction Fragment (TRF) length (Perrem et al., 2001), APB detection (Henson et al., 2005), and immunoprecipitation-TRAP (Pickett et al., 2009) were performed essentially as previously described, with the latter utilizing conventional PCR detection of products.

Immunoblotting

After immunoblotting (as described by Jiang et al., 2005), membranes were probed with mouse anti-green fluorescent protein (BD Bioscience), rabbit anti-RAD51 (Calbiochem), rabbit anti-SMC5 (Bethyl Laboratory) and rabbit anti-MMS21 (from Dr R Potts).

Retroviral Infections, Cloning and Short Interfering RNAs

Retroviral vector pLXSN-YFP-Sp100 was created by cloning EYFP-Sp100 (from Dr. David Spector) into the multiple cloning site of pLXSN (Clontech). Equimolar amounts of pLXSN-YFP-Sp100 (or pLXSN only), pVPack-GP (gag-pol expression vector; Statagene) and pMD2-VSVG envelope vector (from Dr Luigi Naldini), totaling 16 µg DNA, were cotransfected into 293T cells in a 75 cm² flask with Fugene 6 (Roche). Supernatant containing virus was harvested at 48 and 72 hr, filtered through a 0.45 µm Ministart filter (Sartorius) and concentrated 50-fold in a 100,000 MWCO Vivaspin-20 concentrator (Sartorius). 150 µl fresh concentrate in 1 ml DMEM with 8 µg/µl polybrene was added to exponentially growing IIICF/c cells in a 6-well plate.

Cells were treated with short interfering RNAs (siRNAs) with jetPRIME (Polyplus-Transfection) according to the manufacturer's instructions. The siRNA oligonucleotides used were specific to SMC5 (5'-GAAGCAAGAUGUUAUA-GAAdTdT-3') (SEQ ID NO:5), MMS21 (5'-CUCUG-GUAUGGACACAGCUdTdT-3') (SEQ ID NO:6) and RAD51 (validated siRNA; QIAGEN; SI02663682).

Data Analysis

All analyses were blinded with respect to previous results and patient data. Linearity of CC Assay was assessed with linear regression analysis. CC Assay distributions were compared by the two-tailed t-test or Mann-Whitney test. Error bars represent the SEM.

Example 1

Partially Double-Stranded Telomeric Circles can be Detected in ALT[+] Cells by Rolling Circle Amplification The inventors have developed an assay for the detection of partially double-stranded telomeric circles that uses rolling circle amplification. As exemplified herein the assay (hereinafter "CC assay") can be used, for example, to detect C-circles, by φ29-mediated extension of incomplete G-strand (linear strand) segments of the circles, thereby producing long telomeric ssDNA concatemers (see FIG. 1).

Figure 2:
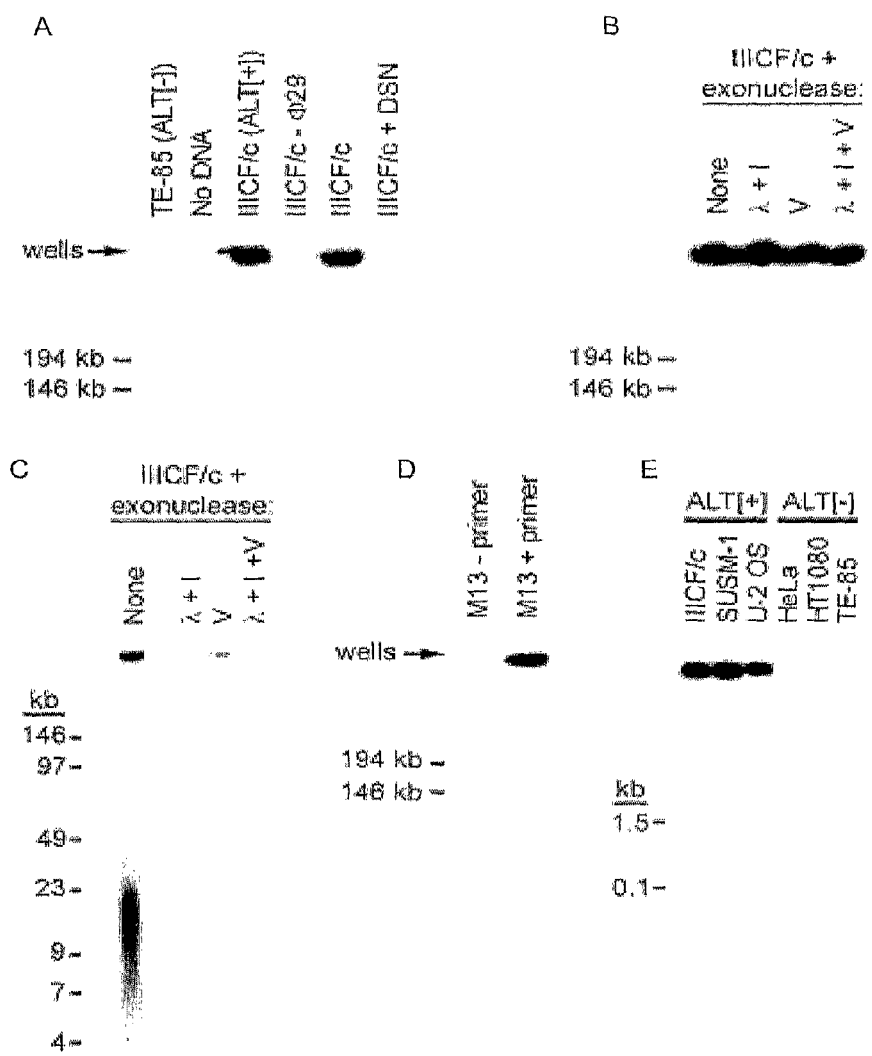
FIG. 2 illustrates the detection of C-circles in ALT[+] cells. A, C-circle (CC) Assay of 30 ng genomic DNA from ALT[+] IIICF/c cells, but not TE-85 ALT[−] cells, produced G-strand products that migrated minimally from the wells after gel electrophoresis, and were not detected when genomic DNA or φ29 DNA polymerase was omitted, or when DNA was pre-treated with Duplex Specific Nuclease (DSN). Positions of double stranded (ds)DNA markers are shown. B and C, 2 μg of restriction enzyme-treated IIICF/c DNA was digested with Exonuclease λ, I and/or V and 1.5% was subjected to the CC Assay (B) and the remainder subjected to Terminal Restriction Fragment (TRF) analysis (C). D, RCA of 100 pg M13 bacteriophage circular single-stranded (ss)DNA with and without including a primer. For (D) only, the reaction included dCTP and product was detected with an M13 specific probe. E, CC Assay of 30 ng genomic DNA from ALT[+] IIICF/c, SUSM-1 and U-2 OS cells, and ALT[−] HeLa, HT1080 and TE-85 cells is shown.

The CC Assay was performed using 30 ng genomic DNA and, after agarose gel electrophoresis, products were detected in ALT[+] IIICF/c cells, but not ALT[−] TE-85 cells (see FIG. 2A).

The CC Assay substrates in IIICF/c cells were (i) telomeric, as evidenced by dCTP being unnecessary for RCA, and by the products being detected with a telomeric G-strand specific probe, (ii) partially double-stranded, as shown by their self-priming ability and destruction by Duplex Specific Nuclease (DSN; FIG. 2A), which digests double-stranded but not single-stranded (ss)DNA, and (iii) circular, as evidenced by the finding that Exonucleases λ, I and V do not diminish the CC Assay products (FIG. 2B) despite degrading most of the linear telomeric DNA (FIG. 2C). A circular template is also required to produce high molecular weight products by rolling circle amplification (FIG. 2A), like those generated from M13 circular ssDNA (FIG. 2D).

By including dCTP in the CC Assay and probing with a telomeric C-strand-hybridizing probe, end-labelled $^{32}$P-(TTAGGG)$_3$, G-circles were also detected in the ALT[+] cell lines IIICF/c, Saos-2 and U-2 OS but not the telomerase[+] cell lines HeLa, MG63 and TE-85. The G-circle levels detected were 100-fold less than C-circle levels in the ALT[+] cell lines (using denatured plasmid containing 1.6 kb of telomeric sequence to calibrate the C-strand- and G-strand-hybridising probes).

The lack of any lower molecular weight products from the CC Assay performed on ALT[+] and ALT[−] cells (FIG. 2E) indicates that dot blotting is suitable for quantitation.

Figure 3:
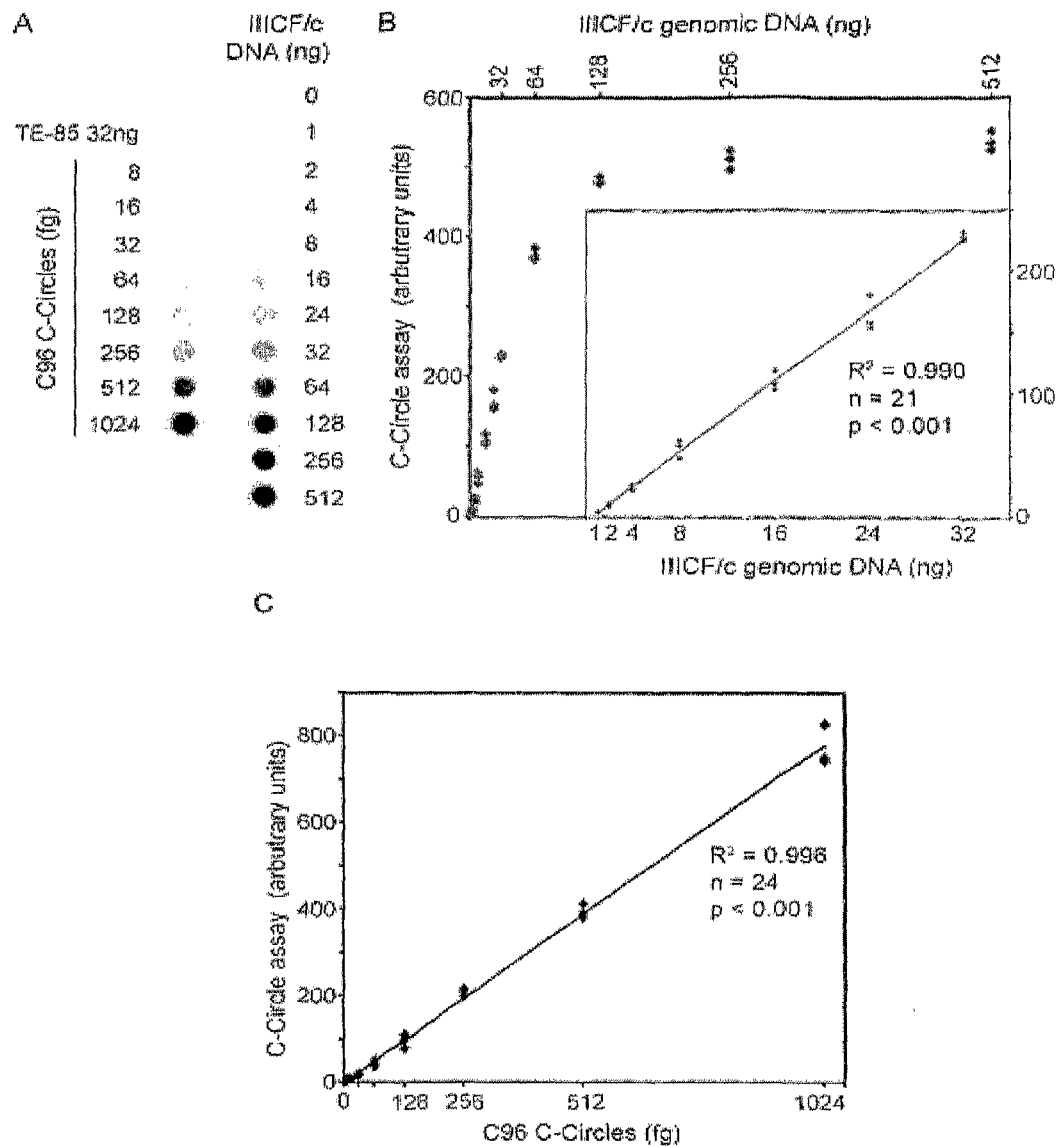
FIG. 3 illustrates the sensitivity and linearity of CC Assay. A, Dot blot of the CC Assay tested with serial dilutions of ALT[+] IIICF/c genomic DNA and C96 (96 nucleotide) C-circles. CC Assay levels for IIICF/c DNA (B) and C96 C-circles (C) are plotted with each point representing one assay. Linear regression analysis was performed for the range of IIICF/c genomic DNA of 1-32 ng (B inset) and C96 C-circles of 8-1024 fg (C) and the lines of best fit drawn.

The inventors also evaluated the CC Assay on serial dilutions of ALT[+] IIICF/c genomic DNA and C96, a C-circle containing 96 nucleotides (FIG. 3). The signal from 1 ng ALT[+] genomic DNA (100 IIICF/c cell equivalents) exceeded that from the no DNA and ALT[−] controls. CC Assay levels were linearly proportional to IIICF/c DNA over an 32-fold range of 1-32 ng ($R^2$=0.990, $p<0.001$; FIG. 3B).

The CC Assay was also linearly proportional to 8-1024 fg, a 128-fold linear range, of pure C96 C-circles ($R^2$=0.996, $p<0.001$; FIG. 3C). 20 ng IIICF/c genomic DNA had a CC Assay signal equivalent to 180 fg C96 C-circles, implying that there are ~1000 C-circles per IIICF/c cell. The actual number may be smaller if the presumably larger C-circles have multiple priming sites or allow better access than C96 to φ29.

Example 2

Partially Double-Stranded Telomeric Circles are Specific for ALT

Figure 4:
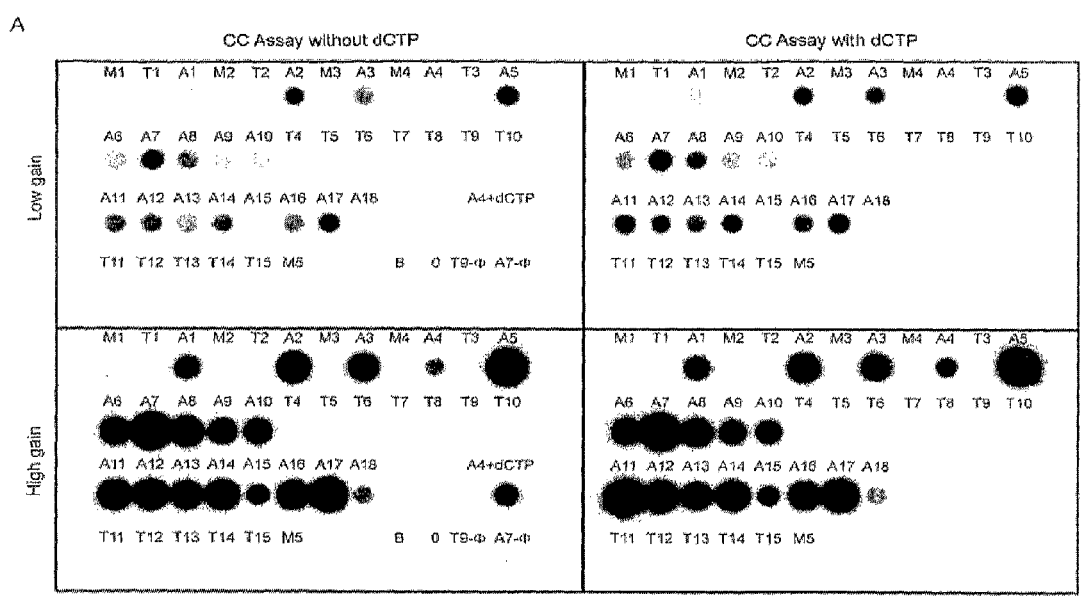
FIG. 4 illustrates that the CC Assay is specific for ALT. Genomic DNA (30 ng) from 18 ALT[+] cell lines (A1-18), 15 telomerase[+] cell lines (T1-15), 5 mortal cell strains (M1-5) were subjected to the CC Assay, without and with dCTP in the polymerase reaction. Individual cell lines/strains are identified in Table 1. A, Representative dot blots are shown with low and high gain to allow comparison of strong and weak levels, respectively. An extra sample of A4, but with dCTP (A4+dCTP) was included in experiments without dCTP to calibrate them to experiments with dCTP. Controls: B, buffer only; 0, No DNA; −φ, φ29 omitted. B, Mean values are plotted on a logarithmic scale, according to telomere maintenance mechanism. The ALT[+] average, 75.2 Arbitrary Units (AU) (horizontal bar), was significantly higher than for telomerase [+] cells, 0.10 AU ($p<0.001$), and mortal cell strains 0.11 AU ($p=0.007$). C, The ratio of CC Assay with dCTP and without dCTP for the ALT[+] cell lines is plotted with the outlier, A4, indicated. The rest of the ALT[+] cell lines are clustered with the horizontal bar indicating their average ratio. D, CC Assay on 32 ng genomic DNA from HeLa cells over-expressing hTR at population doubling (pd)211 (HeLa hTR) that had a substantial increase in telomeric dsDNA circles compared to HeLa expressing vector only (HeLa Vector; pd211) or untreated HeLa cells. E, Mean±Standard Error of the Mean (SEM) (n=3) is plotted. SEM was not applicable for IIICF/c that was used to calibrate the triplicate CC Assays.
Figure 4:
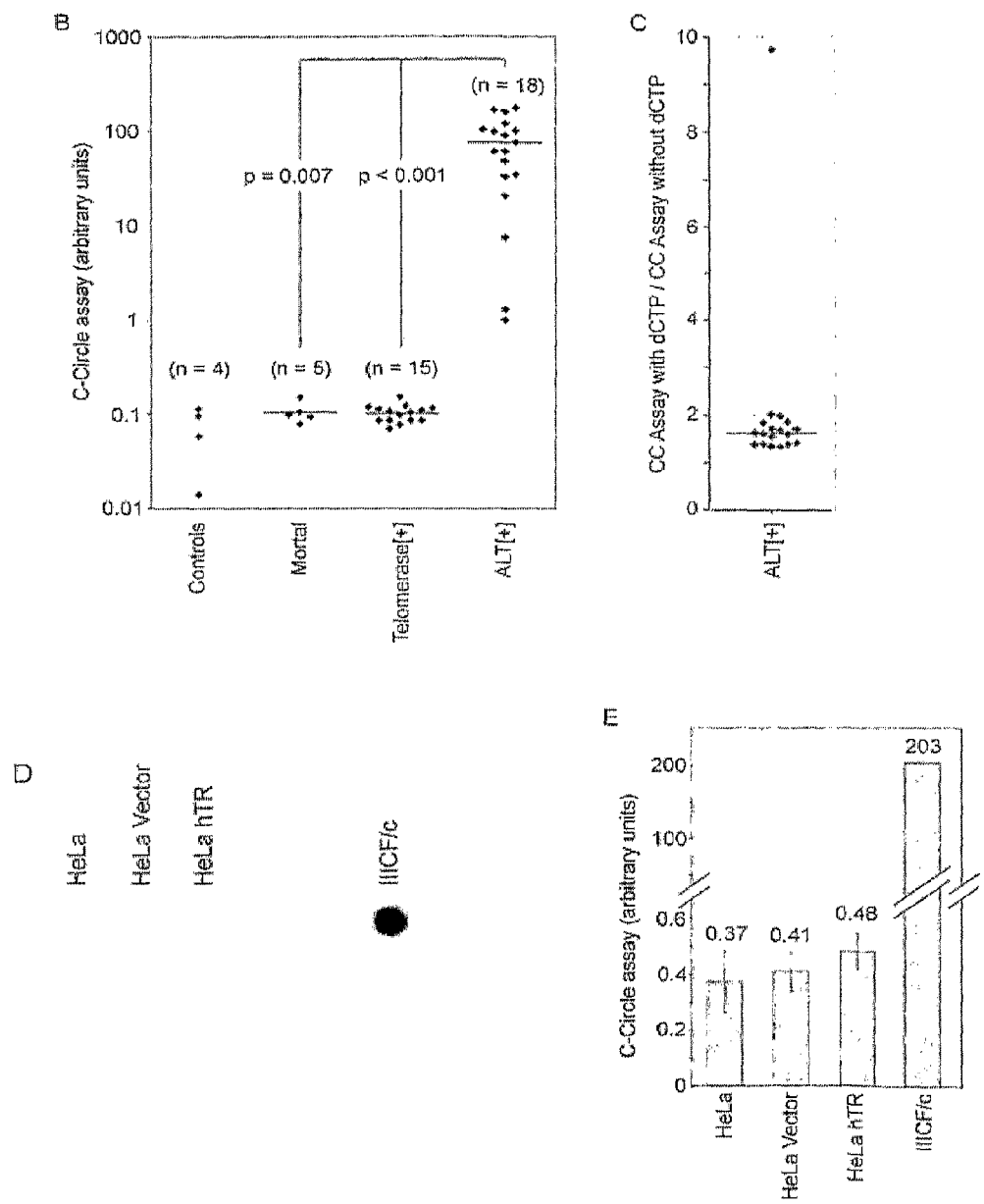

The inventors assayed 18 ALT[+] cell lines and an ALT[−] group consisting of 15 telomerase[+] cell lines and five mortal cell strains using the CC Assay described in Example 1. Results are shown in Table 1 and FIG. 4A.

TABLE 1

Cell Line/Strain CC Assay Results

| Symbol[a] | Cell Line/Strain[b] | CC Assay without dCTP | | CC Assay with dCTP | |
|---|---|---|---|---|---|
| | | mean | SEM | mean | SEM |
| Related cell strains/lines | | | | | |
| M1 | JFCF-6 | 0.15 | 0.009 | 0.20 | 0.009 |
| T1 | JFCF-6/T.1P | 0.07 | 0.013 | 0.06 | 0.026 |
| A1 | JFCF-6/T.1R | 20.6 | 1.1 | 38.1 | 3.5 |
| M2 | MRC-5 | 0.08 | 0.006 | 0.10 | 0.024 |
| T2 | MRC5-V1 | 0.09 | 0.007 | 0.04 | 0.020 |
| A2 | MRC5-V2 | 119 | 1.3 | 166 | 8.84 |
| M3 | IIICF | 0.10 | 0.007 | 0.20 | 0.028 |
| A3 | IIICF/c | 60.9 | 1.6 | 104 | 6.11 |
| M4 | WI-38 | 0.11 | 0.010 | 0.17 | 0.009 |
| A4 | WI38-VA13/2RA | 1.30 | 0.020 | 12.7 | 1.0 |
| T3 | BET-3K | 0.09 | 0.008 | 0.15 | 0.024 |
| A5 | BET-3M | 166 | 4.4 | 223 | 14 |
| Tumor cell lines | | | | | |
| A6 | U-2 OS | 47.9 | 0.33 | 67.6 | 6.3 |
| A7 | SAOS-2 | 176 | 1.9 | 244 | 19 |

TABLE 1-continued

Cell Line/Strain CC Assay Results

| Symbol[a] | Cell Line/Strain[b] | CC Assay without dCTP | | CC Assay with dCTP | |
|---|---|---|---|---|---|
| | | mean | SEM | mean | SEM |
| A8 | G-292 | 89.2 | 3.4 | 138 | 6.6 |
| A9 | SK-LU-1 | 34.8 | 0.81 | 59.6 | 3.1 |
| A10 | DOS16 | 33.0 | 0.75 | 44.3 | 2.0 |
| T4 | TE-85 | 0.09 | 0.006 | 0.04 | 0.014 |
| T5 | MG-63 | 0.10 | 0.004 | 0.17 | 0.008 |
| T6 | SJSA-1 | 0.11 | 0.008 | 0.14 | 0.010 |
| T7 | A549 | 0.15 | 0.001 | 0.20 | 0.007 |
| T8 | HT1080 | 0.11 | 0.005 | 0.16 | 0.014 |
| T9 | HeLa | 0.12 | 0.011 | 0.15 | 0.015 |
| T10 | WMM1175 | 0.12 | 0.014 | 0.15 | 0.012 |
| Cell strain and in vitro immortalized cell lines | | | | | |
| A11 | SUSM-1 | 100 | 0.89 | 203 | 9.9 |
| A12 | KMST-6 | 102 | 1.4 | 165 | 6.7 |
| A13 | GM847 | 60.4 | 2.4 | 101 | 6.3 |
| A14 | GM0637 | 97.4 | 2.4 | 183 | 5.9 |
| A15 | MeT-4A | 7.51 | 0.22 | 14.9 | 0.83 |
| A16 | AT1BR44neo | 76.1 | 0.77 | 125 | 6.1 |
| A17 | W-V | 160 | 1.2 | 223 | 15 |
| A18 | AG11395 | 1.00 | 0.027 | 1.61 | 0.12 |
| T11 | GM639 | 0.11 | 0.44 | 0.08 | 0.019 |
| T12 | 293T | 0.09 | 0.002 | 0.11 | 0.011 |
| T13 | F80-hTERT/K1 | 0.10 | 0.009 | 0.10 | 0.006 |
| T14 | AT22IJE-T | 0.08 | 0.001 | 0.09 | 0.013 |
| T15 | MeT-5A/6TGR-B | 0.12 | 0.017 | 0.13 | 0.007 |
| M5 | HFF5 | 0.09 | 0.008 | 0.09 | 0.008 |
| Controls | | | | | |
| B | Buffer, no reaction | 0.01 | 0.004 | | |
| 0 | Reaction, No DNA | 0.06 | 0.002 | | |
| T9-Φ | HeLa-Φ29 | 0.10 | 0.016 | | |
| A7-Φ | SAOS-2-Φ29 | 0.11 | 0.007 | | |

[a]M = mortal. T = Telomerase[+]. A = ALT[+]. Symbols/numbers correspond to those in FIG. 4.
[b]Cells were cultured in DMEM supplemented with 10% fetal bovine serum (FBS), except epithelial and mesothelial cells which were cultured in LHC-9 and LHC-MM + 3% FBS, respectively (Biosource), in flasks coated with collagen and fibronectin.

The average CC Assay value for ALT[+] cells, 75.2 arbitrary units (AU), was significantly greater than for either the telomerase[+] (0.10 AU, p<0.001) or mortal cells (0.11 AU, p=0.007) (FIG. 4B). This 750-fold difference clearly distinguishes ALT[+] from ALT[−] cells. The two ALT[+] cell lines with low outlying CC Assay levels still had values 7-fold greater than the maximum ALT[−] level. Results for ALT[−] cells were similar to assay background levels in controls without Φ29 DNA polymerase or without DNA (FIG. 4B, Table 1).

The two ALT[+] cell lines with low outlying levels, AG11395 and WI38-VA13/2RA are SV40 in vitro-immortalised cell lines. All ALT[+] tumor-derived cell lines had CC Assay levels>100-fold higher than the highest ALT[−] level. AG11395 is unusual in that it contains SV40 sequence in its telomeres and lacks APBs. WI38-VA13/2RA had a 9.7-fold higher CC Assay level when dCTP was included in the reaction, significantly greater than the 1.6-fold average increase in the other ALT[+] cell lines (p<0.001; FIG. 4C). This suggests that WI38-VA13/2RA contains significantly more variant telomeric repeats or non-telomeric DNA in its C-circles than other ALT[+] cells, consistent with telomere sequencing data that detected increased levels of TCAGGG repeats in this cell line (Varley et al., 2002). The data indicate a CC Assay level of 5× the ALT[−] control is an appropriate threshold for ALT activity. Inclusion of dCTP in the assay is optional.

The inventors also tested the CC-Assay on the C3-c16 clone of WI38-VA13/2RA, expressing exogenous hTR and catalytically-inactive hTERT, that lost ALT characteristics of APBs, long telomeres and t-circles but continued telomere maintenance without reactivating telomerase (Cerone et al., 2005). C3-c16 had increased C-circles and fewer non-canonical telomeric repeats than parental WI38-VA13/2RA cells (data not shown). In C3-c16, like AG11395 cells, C-circles remained despite loss of other ALT markers, indicating C-Circles are more tightly linked to ALT.

It is possible that ALT encompasses a variety of mechanisms. ALT[+] cell lines from a wide range of origins were tested, including osteosarcomas, a lung adenocarcinoma, and a leiomyosarcoma, and cells of fibroblastic, epithelial and mesothelial origins immortalized in vitro spontaneously, virally, chemically and by γ-irradiation. These were compared with ALT[−] cell lines and strains that were closely matched or related. C-circles were found to be ubiquitous among ALT[+] cell lines.

There is evidence that double-stranded t-circles are generated in both ALT[+] and ALT[−] cells by t-loop homologous recombination (Wang et al., 2004). These t-circles are likely nicked in both strands and thus should not be a significant substrate for the CC Assay, however the inventors sought to formally exclude the possibility that t-circles could be processed into partially double-stranded telomeric circles in ALT[−] cells, affecting the specificity of the CC Assay for ALT activity. ALT[−] Hela cells transfected with hTR (HeLa hTR) have substantial levels of t-circles at pd211. The CC Assay level for HeLa hTR (pd211) was not significantly different from HeLa cells transfected with vector only, also at pd211, or HeLa (FIG. 4D, E), and was 400-fold lower than the ALT[+] control. This indicates that the CC Assay is not significantly affected by ALT-independent t-circle formation.

Example 3

Figure 5:
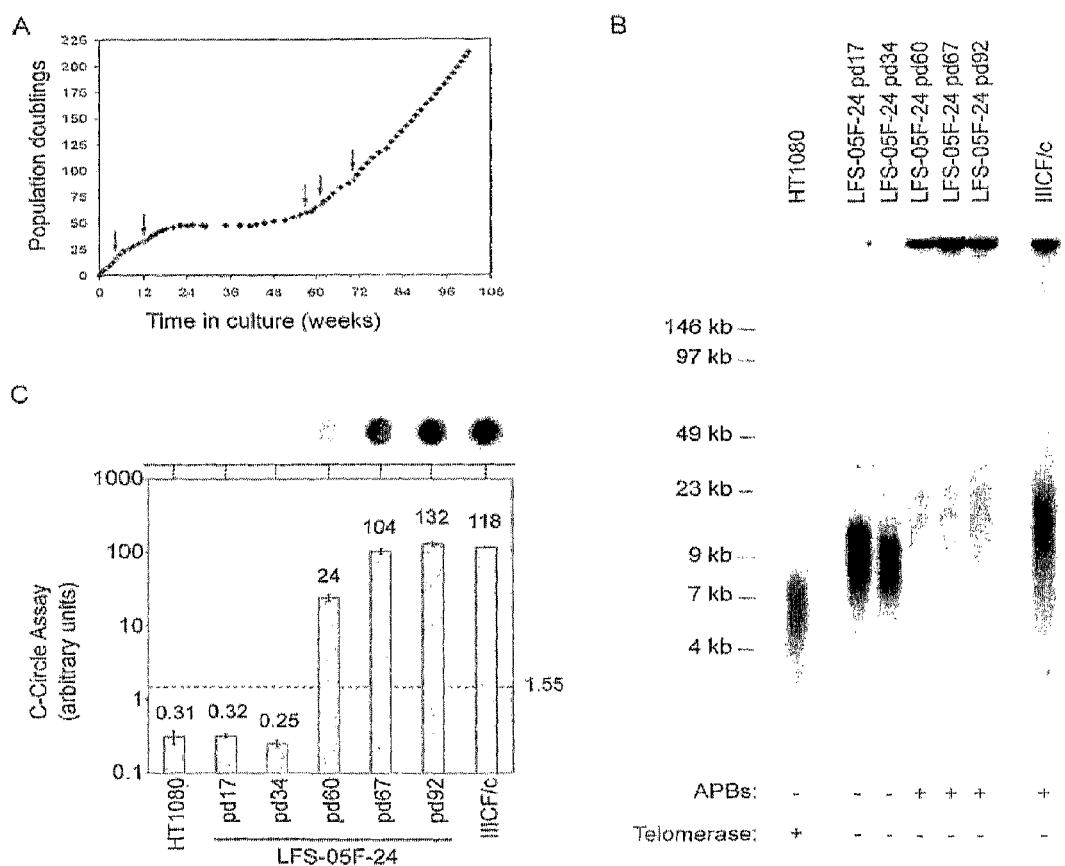
FIG. 5 illustrates that C-circles appear upon activation of ALT. A, Growth curve of LFS-05F-24 fibroblasts derived from a Li-Fraumeni Syndrome patient, cultured for >200 pd with crisis occurring from pd48-50 (arrows). B and C, Genomic DNA extracted at pd17, 34, 60, 67 and 92 (arrows in A) was examined by TRF analysis (2 (B) and by CC Assay (16 ng) (C), and compared to HT1080 telomerase[+] cells, and IIICF/c ALT[+] cells. TRF analysis (B) showed long heterogeneous telomeres after crisis (pd60-92), similar to IIICF/c ALT[+] cells. ALT-associated PML Bodies (APBs) were detected in post- but not pre-crisis cells (B). Telomere Repeat Amplification Protocol (TRAP) analysis (B) detected no telomerase activity at any time point. CC Assay results are plotted as mean±SEM, n=3, on a logarithmic scale (C) with a representative dot blot above the graph. IIICF/c was used to calibrate the triplicate CC Assays. The dotted horizontal line at 1.55 AU represents 5× the ALT[−] HT1080 level, and the threshold for the CC Assay to be positive for ALT activity.

Partially-Double-Stranded Telomeric Circles are Rapidly Responsive to Changes in ALT Activity To determine if partially double-stranded telomeric circles can be detected when ALT is first activated, the inventors examined cultures of Li-Fraumeni Syndrome skin fibroblasts (LFS-05F-24) that underwent spontaneous immortalization in culture (FIG. 5A). Telomere length decreased (FIG. 5B; pd17 and pd34) prior to crisis at pd48. At pd60, the cells were telomerase[−], positive for APBs, and had long heterogeneous telomeres that were maintained (FIG. 5B), indicating they had become ALT[+]. CC Assay of pre-crisis LFS-05F-24 cells (pd17 and pd34; FIG. 5C) was negative for ALT (below the threshold of 5× the ALT[−] control). CC Assay was positive immediately after the ALT[+] cells emerged from crisis (pd60; FIG. 5C) and remained positive (pd67 and pd92).

Figure 6:
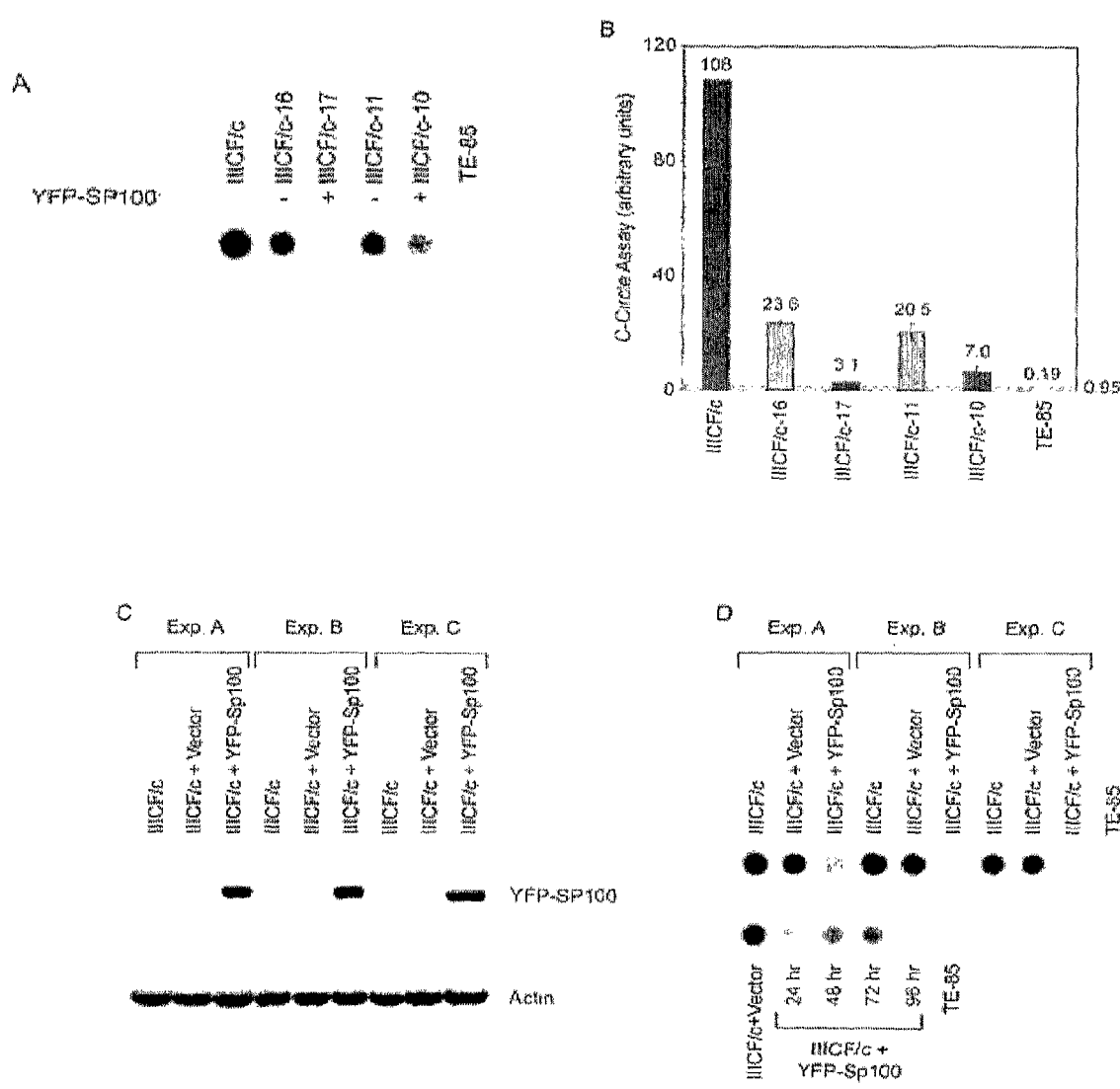
FIG. 6 illustrates that C-circles disappear rapidly when ALT is inhibited. A and B, ALT activity was inhibited in IIICF/c clones, IIICF/c-17 and IIICF/c-10, expressing full-length Yellow Fluorescent Protein (YFP)-Sp100 fusion protein, but not those, IIICF/c-16 and IIICF/c-11, expressing YFP-Sp100 deletion mutants. CC Assay (A) of 16 ng genomic DNA from these clones and ALT[−] TE-85 cells was graphed (B), as mean±SEM, with the horizontal dashed line at 0.95 AU representing 5× level of ALT[−] control. C-F, IIICF/c cells were transiently infected with a YFP-Sp100 expression construct in three independent experiments (A-C). Expression of YFP-Sp100 48 hrs after infection was confirmed by immunoblotting (c) with anti-YFP antibody. CC Assay of 16 ng DNA (D; upper row) was performed in triplicate for each independent experiment and plotted (E) as mean±SEM. The combined experiments (F; n denotes the number of independent experiments) showed YFP-Sp100 expression resulted in a significantly lower CC Assay level, 34.6 AU, than vector alone, 284 AU (p=0.007). G, Triplicate means of CC Assay (lower row) on 16 ng DNA from IIICF/c cells harvested 24-96 hr after infection with YFP-Sp100 and ALT[−] control, TE-85.
Figure 6:
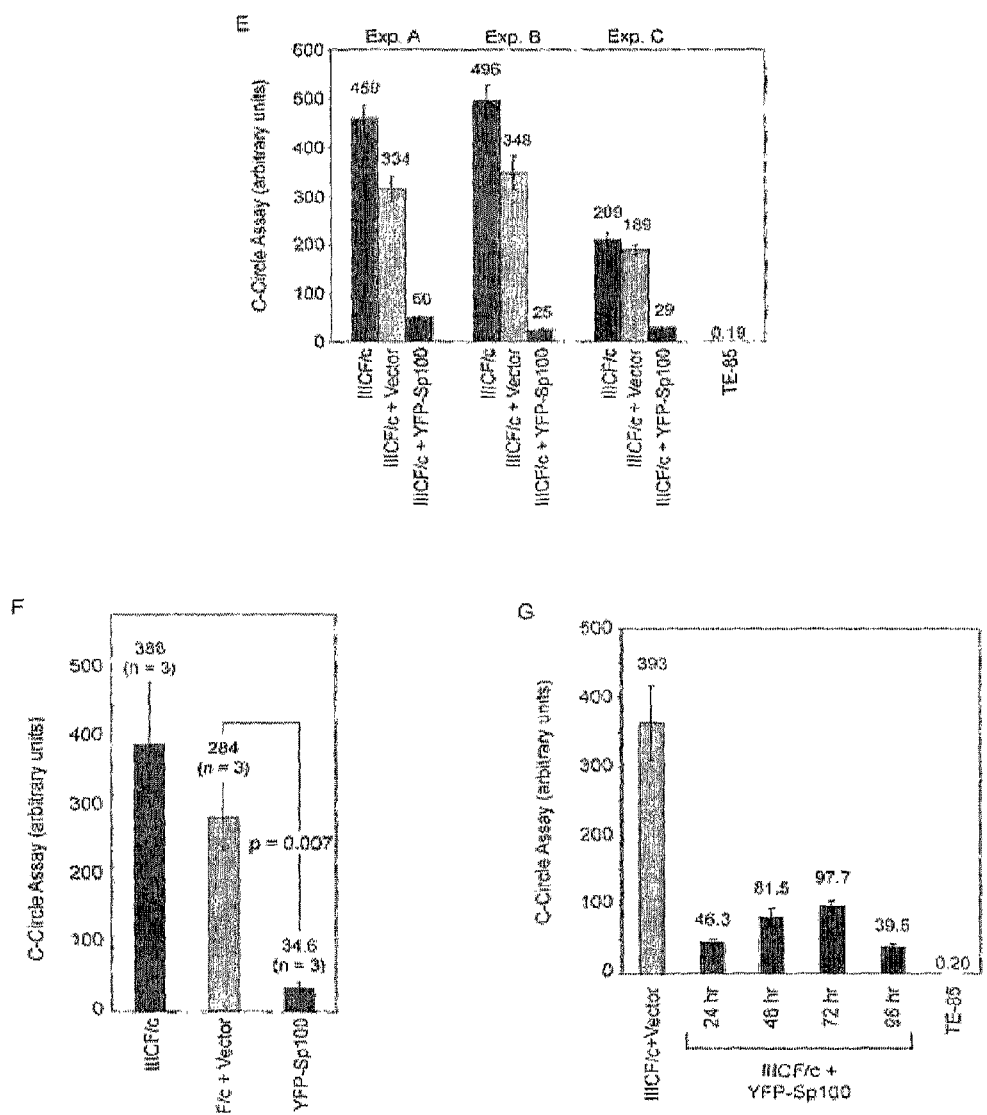

It has been shown that over-expressing YFP-Sp100 fusion protein in IIICF/c clones IIICF/c-10 and IIICF/c-17 inhibited ALT activity, whereas clones IIICF/c-11 and IIICF/c-16 that expressed YFP-Sp100 deletion mutants retained ALT activity (Jiang et al., 2005). In the present study IIICF/c-10 and IIICF/c-17 had CC Assay levels 3- and 7-fold lower, respectively, than the control clones, IIICF/c-11 and IIICF/c-16 (FIGS. 6A, B; all clones were sampled at pd41). The CC Assay detected residual ALT activity in IIICF/c-10 and IIICF/c-17, consistent with these other evidences that these clones retain some ALT activity (Jiang et al., 2005). IIICF/c-10 had 1.5-fold more APBs than IIICF/c-17, a telomere attrition rate 1.7-fold slower, and 2.3-fold more C-circles. C-circle levels were therefore proportional to ALT activity.

To determine how long partially double-stranded telomeric circles persist after inhibition of ALT, the inventors infected IIICF/c cells with YFP-Sp100 retrovirus twice, at 48 hr and 24 hr before harvesting. Infections were performed in three independent experiments, YFP-Sp100 expression was confirmed by immunoblotting (FIG. 6C), and 16 ng genomic DNA from each independent experiment was assayed for C-circles (FIG. 6D, E). CC Assay results for YFP-Sp100-infected cells (average 34.6 AU) showed 88% reduction compared to vector-infected controls (284 AU, p=0.007; FIG. 6F). This represents an almost complete suppression of partially double-stranded telomeric circles, because FACS analysis showed that only 90% of the cells expressed YFP (data not shown). A further experiment (FIG. 6G) showed that the CC Assay could detect the inhibition of ALT activity 24 hr after a single infection with YFP-Sp100 (88% reduction of CC Assay levels) and this inhibition was maintained for at least 96 hr.

To confirm rapid reduction in C-circle levels with ALT inhibition, the inventors assayed SUSM-1 ALT[+] cells 72 hr after knockdown of the SMC5/SMC6/MMS21 complex that has been shown to maintain telomere length in ALT[+] cancer cells (Potts and Yu, 2007). SMC5 or MMS21 siRNAs caused 50% reduction in CC Assay levels compared to siRAD51 and untreated controls (data not shown). RAD51 is a homologous recombination protein not required for ALT.

Example 4

ALT[+] Tumours Correlate with Partially Double-Stranded Telomeric Circles in Blood Cancer-derived DNA can be detected in plasma. Cancer patients typically have 0.1-1 µg extracellular DNA/ml plasma, in contrast to 10 ng/ml in normal individuals. The inventors used the CC Assay to test archived blood specimens from pediatric osteosarcoma patients whose tumour ALT status had been determined previously by detecting APBs (Henson et al., 2005).

Figure 7:
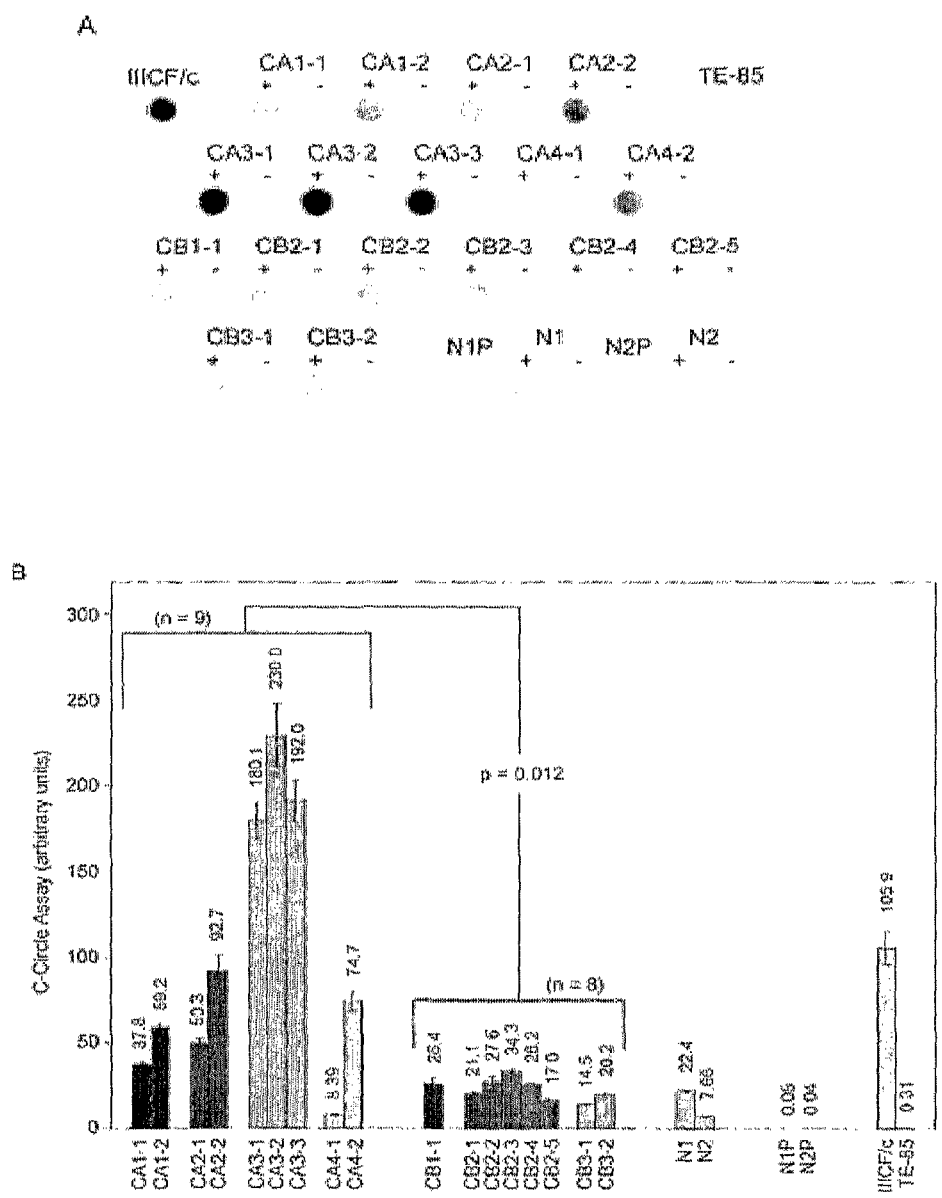
FIG. 7 illustrates an increase in C-circles in the blood of ALT[+] osteosarcoma patients. A, The CC Assay was tested on 2% of the exonuclease treated DNA isolated from 2 ml whole blood from seven pediatric osteosarcoma patients and two normal controls, N1 and N2. Four patients had ALT[+] osteosarcomas, CA1-CA4 and three ALT[−], CB1-CB3 (Henson et al., 2005). Patients had multiple samples collected at different time-points after diagnosis. The CC Assay was also performed on 20% of DNA isolated from plasma purified from 2 ml of whole blood from the normal controls, N1P and N2P, and 16 ng genomic DNA from ALT[+] IIICF/c cells and ALT[−] TE-85 cells. CC Assays on whole blood were performed with and without φ29, + and −, respectively. B, CC Assay results are graphed as mean±SEM, n=3. For whole blood samples the results without φ29 were first subtracted from the result with φ29. The average CC Assay level for the nine blood samples from ALT[+] patients, 102.8 AU was significantly higher than the eight blood samples from ALT [−] patients, 23.4 AU (p=0.012). C and D, CC Assay was tested on a serial dilution of patient blood specimen CA3-3 (C) and plotted (D) with each point representing one experiment. Linear regression analysis was performed for the range of 0.4%-2% CA3-3 DNA and the line of best fit drawn.
Figure 7:
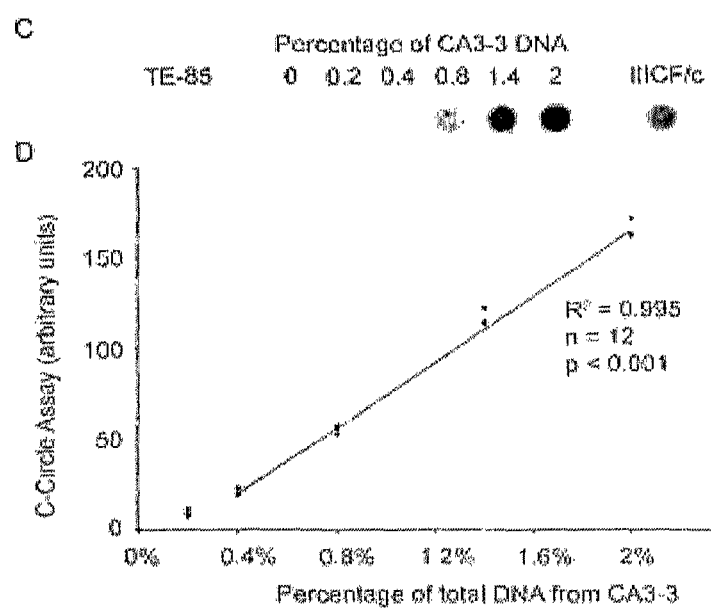

DNA was extracted directly from whole blood, because prior storage at −80° C. precluded plasma isolation. The blood contained on average 46 µg DNA/2 ml sample (range 12-159 µg), presumably mainly of leukocyte origin, and 100- to 1,000-fold more than the expected amount of cancer-derived DNA. Microgram quantities of genomic DNA inhibit the CC Assay (data not shown), so the whole blood DNA was digested with Exonuclease λ, I and V until <100 ng dsDNA and <400 ng ssDNA remained, then tested 2% of the total remaining DNA by CC Assay (FIG. 7A, B). Background signal was determined by omitting φ29 and subtracted from the CC Assay result. Two samples, CB2-5 and CB3-1, had both the highest DNA yields (159 µg and 104 µg, respectively) and the highest level of background (FIG. 7A). This is consistent with the background arising from G-strand telomeric ssDNA remaining after exonuclease digestion.

The average CC Assay result for nine whole blood samples collected from four ALT[+] osteosarcoma patients (102.8 AU; 95% CI, 51.8-153.8), was higher than that for eight samples from three ALT[−] osteosarcoma patients (23.4 AU; 95% CI, 19.0-27.9; p=0.012), and for samples from two normal volunteers (15.0 AU; 95% CI, 0.6-29.5). The CC Assay levels for all ALT[+] patients eventually rose to levels well above the distribution of levels for the ALT[−] osteosarcoma patients (more than five standard deviations above the ALT[−] mean). To confirm the CC Assay retained linearity in the working range for DNA from whole blood, it was tested on CA3-3 DNA (FIG. 7C). The CC Assay was linearly proportional to 0.4-2% of total CA3-3 DNA ($R^2$=0.995, p<0.001; FIG. 7D).

Plasma was also obtained from normal volunteers, and an average of 31 ng DNA was extracted from 2 ml, No C-circles were detected when 20% of the total plasma DNA was tested by CC Assay (FIG. 7A, B). This lower background suggests that CC Assay using plasma will yield a better signal-to-noise ratio than using whole blood. The CC Assay detected C-circles in similar amounts of plasma from Balb/c nu/nu mice bearing ALT[+] tumors (data not shown).

Example 5

CC Assay Distinguishes ALT Status in a Diverse Range of Tumour Types

Figure 8:
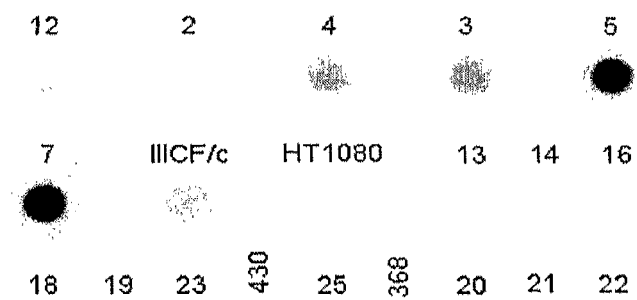
FIG. 8 shows CC Assay results for soft tissue sarcoma (STS) tumours. The CC Assay was performed on 18 STS and typical ALT[+] (IIICF/c) and telomerase[+] (HT1080) immortal cell lines. The dot blot of the CC Assay products is shown.

The ability of the CC Assay to detect ALT activity when performed on DNA extracted from tumour samples was tested on 88 frozen tumour specimens. This consisted of 16 Soft Tissue Sarcoma (STS) tumours, which had their ALT status determined by the APB assay (Henson et al 2005), and 27 glioblastoma multiforme tumours, 43 mesothelioma tumours and two xenografts which all had their ALT status determined by the TRF assay (Dr A Au and Prof Reddel, unpublished results). The STS included leiomyosarcomas, malignant fibrous histiocytomas, synovial sarcomas, fibrosarcomas, rhabdomyosarcomas and chondrosarcomas. Each of the two xenograft tumours were grown in separate immunodeficient mice after subcutaneous injection of cells from human ALT[+] and ALT[−] cell lines, respectively. Frozen tumour samples, 10-40 mg, were homogenised in 440-1720 µl lysis buffer (50 mM Tris-HCl pH 8, 20 mM EDTA, 2% sodium dodecylsulphate) using a plastic pestle. Proteinase K, 400-1600 µg, was added and the sample incubated at 55° C. for 12 hrs with occasional vortexing. Fresh Proteinase K, 400-1600 µg, was then added and the sample incubated at 55° C. for an additional 12 hrs with occasional vortexing. DNA extraction then proceeded as described for cell lines. For the C-circle assay 30 ng of genomic DNA was used The CC Assay results are shown in FIGS. 8, 9 and 10 with the concordance between CC Assay results and prior art shown in Tables 2 and 3 below. To obtain the data shown in Tables 2 and 3, quantitation was performed on CC Assay results using ImageQuant TL v2005 with edge subtraction for background correction. In Table 2 the average result of duplicate CC Assays for each sample is shown. The six STS that were found to be ALT[+] by the APB assay had an average CC Assay level of 277.7 arbitrary units (AU). This was more than 180-fold the average CC Assay level for the STS found to be ALT[−] by the APB assay, 1.5 AU. The CC Assay levels of the ALT[+] STS (by APB assay) was significantly higher than the ALT[−] STS, p=0.015 (independent sample t-test assuming equal variances). The lowest CC assay levels for the ALT[+] STS corresponded to the STS with low levels of APBs. Thus the CC Assay levels reflected the ALT activity level indicated by the APB assay. The lowest CC Assay level for an ALT[+] STS (STS 2, C-circle assay level=7.2 AU) was well above the distribution for the ALT[−] STS, more than ten standard deviations (0.4 AU) higher than the mean ALT[−] STS C-circle level of 1.5 AU. The CC Assay also gave a definitive result where the TRF assay was equivocal (STS 12 and 430).

TABLE 2

Agreement between CC Assay and prior art ALT assays for 16 STS

|  | APB assay | TRF assay | CC Assay (AU) |
|---|---|---|---|
| ALT+ by APB assay | | | |
| 2 | ALT+ (low) | ALT+ | 7.2 |
| 12 | ALT+ (low) | equivocal | 15.4 |
| 4 | ALT+ | ALT+ | 131.0 |
| 3 | ALT+ | ALT+ | 142.3 |
| 5 | ALT+ | ALT+ | 615.6 |
| 7 | ALT+ | ALT+ | 754.9 |
| mean | | | 277.7 |
| ALT− by APB assay | | | |
| 25 | ALT− | ALT− | 0.9 |
| 21 | ALT− | ALT− | 1.1 |
| 22 | ALT− | ALT− | 1.2 |
| 20 | ALT− | ALT− | 1.4 |
| 16 | ALT− | ALT− | 1.4 |
| 13 | ALT− | ALT− | 1.5 |
| 23 | ALT− | ALT− | 1.5 |
| 18 | ALT− | ALT− | 1.9 |
| 14 | ALT− | ALT− | 2.1 |
| 19 | ALT− | ALT− | 2.3 |
| mean | | | 1.5 |
| standard deviation | | | 0.4 |
| Other STS | | | |
| 430 | Not done | equivocal | 1.2 |
| 368 | Not done | ALT− | 1.4 |
| Controls | | | |
| HT1080 | ALT− | ALT− | 0.9 |
| IIICF/c | ALT+ | ALT+ | 74.7 |

Turning to Table 3, the TRF assay and CC Assay (average of duplicates) was performed on DNA extracted from 27 glioblastoma multiforme and 43 mesothelioma tumours (Dr A Au and Prof R Reddel, unpublished results). Only one of these 70 tumours was found to be ALT[+] by the TRF assay, GBM-9, and this was the only tumour that had raised CC Assay levels. For controls, typical ALT[+] (GM847) and telomerase[+] (HCT116) immortal cell lines were used. Tumours formed in immunodeficient mice from ALT[+] cell line IIICF/c-EJ-ras and telomerase+ cell line WM1175 were also tested and only the ALT[+] xenograft had raised CC Assay levels.

TABLE 3

Agreement between CC Assay and TRF assay for ALT in glioblastoma multiforme and mesothelioma tumours

| Sample | TRF assay | CC Assay (AU) |
|---|---|---|
| Glioblastoma Multiforme tumours | | |
| GBM-7 | ALT− | 0.1 |
| GBM-5 | ALT− | 0.1 |
| GBM-14 | ALT− | 0.2 |
| GBM-12 | ALT− | 0.6 |
| GBM-10 | ALT− | 0.8 |
| GBM-2 | ALT− | 0.9 |
| GBM-15 | ALT− | 1.1 |
| GBM-16 | ALT− | 1.1 |
| GBM-13 | ALT− | 1.3 |
| GBM-8 | ALT− | 1.5 |
| GBM-11 | ALT− | 1.7 |
| GBM-6 | ALT− | 1.7 |
| GBM-27 | ALT− | 1.8 |
| GBM-24 | ALT− | 1.9 |
| GBM-21 | ALT− | 1.9 |
| GBM-20 | ALT− | 2.1 |
| GBM-3 | ALT− | 2.1 |
| GBM-18 | ALT− | 2.4 |
| GBM-23 | ALT− | 2.4 |
| GBM-4 | ALT− | 2.6 |
| GBM-17 | ALT− | 2.7 |
| GBM-25 | ALT− | 2.7 |
| GBM-26 | ALT− | 3.0 |
| GBM-22 | ALT− | 3.4 |
| GBM-1 | ALT− | 3.8 |
| GBM-19 | ALT− | 5.0 |
| GBM-9 | ALT+ | 92.4 |
| Mesothelioma tumours | | |
| Meso-17 | ALT− | 0.1 |
| Meso-19 | ALT− | 0.1 |
| Meso-10 | ALT− | 0.1 |
| Meso-39 | ALT− | 0.1 |
| Meso-1 | ALT− | 0.1 |
| Meso-12 | ALT− | 0.1 |
| Meso-33 | ALT− | 0.1 |
| Meso-20 | ALT− | 0.2 |
| Meso-11 | ALT− | 0.2 |
| Meso-29 | ALT− | 0.2 |
| Meso-26 | ALT− | 0.2 |
| Meso-23 | ALT− | 0.2 |
| Meso-37 | ALT− | 0.3 |
| Meso-36 | ALT− | 0.3 |
| Meso-25 | ALT− | 0.3 |
| Meso-9 | ALT− | 0.3 |
| Meso-13 | ALT− | 0.3 |
| Meso-24 | ALT− | 0.4 |
| Meso-42 | ALT− | 0.4 |
| Meso-14 | ALT− | 0.5 |
| Meso-30 | ALT− | 0.5 |
| Meso-6 | ALT− | 0.5 |
| Meso-31 | ALT− | 0.6 |
| Meso-22 | ALT− | 0.6 |
| Meso-7 | ALT− | 0.6 |
| Meso-34 | ALT− | 0.6 |
| Meso-38 | ALT− | 0.6 |
| Meso-32 | ALT− | 0.6 |
| Meso-15 | ALT− | 0.7 |
| Meso-40 | ALT− | 0.7 |
| Meso-16 | ALT− | 0.7 |
| Meso-4 | ALT− | 0.7 |
| Meso-2 | ALT− | 0.7 |
| Meso-3 | ALT− | 0.9 |
| Meso-18 | ALT− | 0.9 |
| Meso-41 | ALT− | 0.9 |
| Meso-28 | ALT− | 1.0 |
| Meso-8 | ALT− | 1.0 |
| Meso-21 | ALT− | 1.0 |
| Meso-27 | ALT− | 1.1 |
| Meso-35 | ALT− | 1.2 |
| Meso-5 | ALT− | 1.2 |
| Meso-43 | ALT− | 2.1 |
| Controls | | |
| ALT− xenograft | ALT− | 0.1 |
| HCT116 | ALT− | 3.4 |
| ALT+ xenograft | ALT+ | 54.1 |
| GM847 | ALT+ | 109.2 |

As shown in Tables 2 and 3, the concordance between the CC Assay and the standard assays for ALT was precise in all 88 tumours tested. The CC Assay clearly distinguished the eight ALT[+] tumours from the 80 ALT-tumours. For the STS tumours, the CC Assay levels were significantly higher in the ALT[+] group compared to the ALT[−] group (p=0.015; independent sample t-test assuming equal variances; Table 2). The average ALT[+] level was more than 180-fold the ALT[−]

level and all ALT[+] tumours had significantly raised CC Assay levels, with the lowest ALT[+] level being more than ten standard deviations outside the ALT[−] distribution of CC assay levels. Thus the CC Assay separated the ALT[+] and ALT[−] STS into distinct groups (FIG. 9). The CC Assay levels also reflected the levels of ALT activity as determined by the APB assay. STS 2 and 12, which had abnormal low levels of APB+ nuclei, also had an order of magnitude lower CC Assay levels than the other ALT[+] STS. The utility of the CC Assay was supported by the finding that it was able to accurately assign ALT status to STS 12, which had an equivocal ALT status by the TRF assay (ALT+ by APB assay; see Table 4).

The above results demonstrate that the CC Assay is applicable to a diverse range of tumour types.

REFERENCES

Bryan, T. M. et al. Telomere elongation in immortal human cells without detectable telomerase activity. *EMBO J.* 14, 4240-4248 (1995).

Bryan, T. M. et al. Evidence for an alternative mechanism for maintaining telomere length in human tumors and tumor-derived cell lines. *Nat. Med.* 3, 1271-1274 (1997).

Collado, M. et al. Tumour biology: senescence in premalignant tumours, *Nature* 436:642 (2005).

Dean, F. B. et al. Rapid amplification of plasmid and phage DNA using Phi 29 DNA polymerase and multiply-primed rolling circle amplification. *Genome Res.* 11, 1095-1099 (2001).

Hakin-Smith, V. et al. Alternative lengthening of telomeres and survival in patients with glioblastoma multiforme, *Lancet* 361, 836-838 (2003).

Henson, J. D. et al. Alternative lengthening of telomeres in mammalian cells. *Oncogene* 21, 598-610 (2002).

Henson, J. D. et al. A robust assay for alternative lengthening of telomeres (ALT) in tumors demonstrates the significance of ALT in sarcomas and astrocytomas. *Clin. Cancer Res.* 11, 217-225 (2005), Henson, J. D. The role of Alternative Lengthening of Telomeres in human cancer. University of Sydney, PhD Thesis/Dissertation (2006).

Jiang, W. Q. et al. Suppression of alternative lengthening of telomeres by Sp100-mediated sequestration of MRE11/RAD50/NBS1 complex. *Mol. Cell. Biol.* 25, 2708-2721 (2005).

Perrem, K. et al. Coexistence of alternative lengthening of telomeres and telomerase in hTERT-transfected GM847 cells. *Mol. Cell. Biol.* 21, 3862-3875 (2001).

Pickett, H. A. et al. Control of telomere length by a trimming mechanism that involves generation of t-circles. *EMBO J.* 28, 799-809 (2009).

Potts, P. R. and Yu, H. The SMC5/6 complex maintains telomere length in ALT cancer cells through SUMOylation of telomere-binding proteins. *Nat. Struct. Mol. Biol.* 14, 581-590 (2007).

Ulaner, G. A. et al. Absence of a telomere maintenance mechanism as a favorable prognostic factor in patients with osteosarcoma. *Cancer Res.* 63, 1759-1763 (2003).

Varley, H. et al. Molecular characterization of inter-telomere and intra-telomere mutations in human ALT cells. *Nat. Genet.* 30, 301-305 (2002).

Villa, R. et al. Multiple mechanisms of telomere maintenance exist and differentially affect clinical outcome in diffuse malignant peritoneal mesothelioma. *Clin. Cancer Res.* 14, 4134-4140 (2008).

Wang, R. C. et al. Homologous recombination generates T-loop-sized deletions at human telomeres. *Cell* 119, 355-368 (2004).

The invention claimed is:

1. A method for determining whether a human cell possesses an active Alternative Lengthening of Telomeres (ALT) mechanism, the method comprising:
   (a) amplifying partially double-stranded C-rich telomeric circles from a DNA sample from a human cell using rolling circle amplification, wherein said amplification uses the partially double-stranded C-rich telomeric circles of the DNA sample as a template and wherein said amplification is performed in the absence of an exogenous primer;
   (b) detecting the amplified partially double-stranded C-rich telomeric circles from step (a); and
   (c) determining that the human cell possesses an active ALT mechanism by the presence of the amplified circles.

2. A method according to claim 1 wherein the partially double-stranded C-rich telomeric circles comprise repeats of the sequence (CCCTAA)$_n$ on a circular strand and comprise the sequence (TTAGGG)$_n$ on a linear strand.

3. A method according to claim 1 wherein a circular and/or a linear strand comprises variant telomeric repeat sequences, mutant telomeric sequences and/or further comprise non-telomeric sequences.

4. A method according to claim 1 wherein the cell is a cancer cell.

5. A method according to claim 1 wherein the cell is derived from a subject suffering from, suspected of suffering from, or predisposed to, a disease or condition associated with abnormal cellular proliferation.

6. A method according to claim 5 wherein the disease or condition is a cancer selected from a sarcoma, a blastoma, a carcinoma, a mesothelioma or an astrocytoma.

7. A method according to claim 1, wherein the method comprises:
   (1) optionally isolating DNA from the cell;
   (2) incubating the DNA in the presence of a DNA polymerase and one or more dNTPs under suitable conditions such that polymerase-mediated extension from a linear strand of the partially double-stranded telomeric DNA generates concatemers of single-stranded telomeric DNA; and
   (3) detecting the concatemers.

8. A method according to claim 7 wherein the concatemers are detected by hybridisation, sequencing, PCR, molecular beacons, or nucleic acid enzymes, or by incorporating suitably labelled dNTPs in incubation step (2).

9. A method according to claim 7 wherein the DNA polymerase is φ29 DNA polymerase.

10. A method according to claim 1 wherein the partially double-stranded C-rich telomeric circles are amplified from a biological sample derived from a subject.

11. A method according to claim 10 wherein the biological sample comprises blood, urine, sputum, pleural fluid, peritoneal fluid, bronchial or bronchioalveolar lavage fluid, or a tissue section.

12. A method according to claim 11 wherein the blood is whole blood, blood serum or blood plasma.

13. A method for determining the level of Alternative Lengthening of Telomeres (ALT) activity in a human cell, the method comprising:
(a) amplifying partially double-stranded C-rich telomeric circles from a DNA sample from a human cell using rolling circle amplification, wherein said amplification uses the partially double-stranded C-rich telomeric circles of the DNA sample as a template, and wherein said amplification is performed in the absence of an exogenous primer;
(b) detecting the amplified partially double-stranded C-rich telomeric circles from step (a); and
(c) determining the level of ALT activity in the human cell by the amount of the amplified circles,
wherein the amount of the amplified circles is indicative of the level of ALT activity in the human cell.

14. A method for determining the Alternative Lengthening of Telomeres (ALT) status of a cancer in a human subject, the method comprising:
(a) obtaining a sample from the subject;
(b) amplifying partially double-stranded C-rich telomeric circles from the sample using rolling circle amplification, wherein said amplification uses the partially double-stranded C-rich telomeric circles of the DNA sample as a template, and wherein said amplification is performed in the absence of an exogenous primer;
(c) detecting the amplified partially double-stranded C-rich telomeric circles from step (b); and
(d) determining the ALT status of a cancer in the human subject,
wherein the presence of the amplified circles is indicative of the human subject having cancer cells possessing ALT activity, and wherein the absence of the amplified circles is indicative of the human subject having cancer cells not possessing ALT activity.

15. A method according to claim 14 further comprising quantifying the level of ALT activity in the cancer cell and/or quantifying the amount or proportion of ALT+ cells in the sample based on the amount of the partially double-stranded C-rich telomeric circles in the sample.

16. A method for diagnosing cancer, or predicting the onset thereof, in a human subject, wherein the cancer displays Alternative Lengthening of Telomeres (ALT) activity, the method comprising:
(a) obtaining a sample from the human subject;
(b) amplifying partially double-stranded C-rich telomeric circles from the sample using rolling circle amplification, wherein said amplification uses the partially double-stranded C-rich telomeric circles of DNA as a template and wherein said amplification is performed in the absence of an exogenous primer;
(c) detecting the amplified partially double-stranded C-rich telomeric circles from step (b); and
(d) diagnosing cancer, or predicting the onset thereof,
wherein the presence and/or amount of the amplified circles is indicative of the human subject having cancer, or the likelihood of the onset of cancer in the human subject.

17. A method according to claim 16 wherein the human subject is suspected of having cancer, is predisposed or otherwise susceptible thereto, has one or more high risk factors for developing cancer, or has a cancer predisposition syndrome.

18. A method for evaluating the efficacy of a treatment regime in a human subject suffering from a cancer displaying Alternative Lengthening of Telomeres (ALT) activity, the method comprising:
(a) treating the subject with a suitable anti-cancer treatment regime for a period sufficient to evaluate the efficacy of the regimen;
(b) obtaining a sample from the subject;
(c) amplifying partially double-stranded C-rich telomeric circles from the sample using rolling circle amplification, wherein said amplification uses the partially double-stranded telomeric circles of DNA as a template, and wherein said amplification is performed in the absence of an exogenous primer
(d) detecting the amplified partially double-stranded C-rich telomeric circles from step (c),
(e) repeating steps (b), (c) and (d) at least once over a period of time;
(f) determining whether the presence and/or amount of the amplified circles changes over the period of time; and
(g) evaluating the efficacy of the treatment regimen in the human subject,
wherein a change in the presence and/or amount of the amplified circles is indicative of a change in disease control in the human subject and the degree of efficacy of the treatment regime.

* * * * *